(12) United States Patent
Guan et al.

(10) Patent No.: US 11,077,092 B2
(45) Date of Patent: Aug. 3, 2021

(54) METHODS OF TREATING DIABETES BY ADMINISTERING A GLUCAGON RECEPTOR ANTAGONIST IN COMBINATION WITH A CHOLESTEROL ABSORPTION INHIBITOR

(71) Applicant: Merck Sharp & Dohme Corp., Rahway, NJ (US)

(72) Inventors: Hong-Ping Guan, Scotch Plains, NJ (US); Jose M. Castro-Perez, New Providence, NJ (US); Harry R. Davis, Berkeley Heights, NJ (US); Samuel E. Engel, New York, NY (US); Douglas G. Johns, Ocean, NJ (US); Songnian Lin, Holmdel, NJ (US); Stephen F. Previs, Branchburg, NJ (US); Thomas P. Roddy, Whitehouse Station, NJ (US); Liangsu Wang, Hillsborough, NJ (US); Sheng-Ping Wang, Annandale, NJ (US); Yusheng Xiong, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 137 days.

(21) Appl. No.: 15/484,508

(22) Filed: Apr. 11, 2017

(65) Prior Publication Data
US 2017/0216250 A1    Aug. 3, 2017

Related U.S. Application Data

(63) Continuation of application No. 14/649,651, filed as application No. PCT/US2013/073780 on Dec. 8, 2013, now abandoned.

(60) Provisional application No. 61/735,304, filed on Dec. 10, 2012.

(51) Int. Cl.
| | |
|---|---|
| *A61P 3/10* | (2006.01) |
| *A61K 31/397* | (2006.01) |
| *A61K 31/435* | (2006.01) |
| *A61K 31/44* | (2006.01) |
| *A61K 31/4184* | (2006.01) |
| *A61K 31/403* | (2006.01) |
| *A61K 31/194* | (2006.01) |
| *A61K 31/404* | (2006.01) |
| *A61K 31/415* | (2006.01) |
| *A61K 9/24* | (2006.01) |
| *A61K 45/06* | (2006.01) |

(52) U.S. Cl.
CPC ............ *A61K 31/397* (2013.01); *A61K 9/209* (2013.01); *A61K 31/194* (2013.01); *A61K 31/403* (2013.01); *A61K 31/404* (2013.01); *A61K 31/415* (2013.01); *A61K 31/4184* (2013.01); *A61K 31/435* (2013.01); *A61K 31/44* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,630,200 | A | 12/1971 | Higuchi |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,631,365 | A | 5/1997 | Rosenblum et al. |
| 5,756,470 | A | 5/1998 | Yumibe et al. |
| 5,767,115 | A | 6/1998 | Rosenblum et al. |
| 5,846,966 | A | 12/1998 | Rosenblum et al. |
| 6,207,822 | B1 | 3/2001 | Thiruvengadam et al. |
| 6,982,251 | B2 | 1/2006 | Ghosal et al. |
| 7,071,181 | B2 | 7/2006 | Davis et al. |
| 7,598,285 | B2 | 10/2009 | Parmee et al. |
| 7,687,534 | B2 | 3/2010 | Stelmach et al. |
| 7,816,557 | B2 | 10/2010 | Conner et al. |
| RE42,461 | E | 6/2011 | Rosenblum et al. |
| 2005/0272794 | A1* | 12/2005 | Parmee ............... C07D 231/12 514/406 |
| 2007/0088070 | A1 | 4/2007 | Parmee et al. |
| 2008/0274947 | A1 | 11/2008 | Jaehne et al. |
| 2011/0165239 | A1 | 7/2011 | Alani et al. |
| 2011/0306624 | A1 | 12/2011 | Lin et al. |

FOREIGN PATENT DOCUMENTS

| | | |
|---|---|---|
| WO | 93/02048 A1 | 2/1993 |
| WO | 2005/065680 A1 | 7/2005 |
| WO | 2005/121097 A2 | 12/2005 |
| WO | 2005/123688 A2 | 12/2005 |
| WO | 2006/014618 A2 | 2/2006 |

(Continued)

OTHER PUBLICATIONS

Engel, S. S., et al. Efficacy and Tolerability of MK-0893, a Glucagon Receptor Antagonist (GRA), in Patients with Type 2 Diabetes (T2DM). Diabetes 60 Suppl 1 (Jul. 2011): A85.*

(Continued)

*Primary Examiner* — Bethany P Barham
*Assistant Examiner* — Peter Anthopolos
(74) *Attorney, Agent, or Firm* — Sarah L. Hooson; Catherine D. Fitch

(57) ABSTRACT

Use of a glucagon receptor antagonist in combination with a cholesterol absorption inhibitor for the treatment of diabetes and related conditions is disclosed.

15 Claims, 17 Drawing Sheets

(56) References Cited

FOREIGN PATENT DOCUMENTS

| | | |
|---|---|---|
| WO | 2006/017055 A2 | 2/2006 |
| WO | 2006/086488 A2 | 8/2006 |
| WO | 2006/102067 A1 | 9/2006 |
| WO | 2006/104826 A2 | 10/2006 |
| WO | 2007/015999 A2 | 2/2007 |
| WO | 2007/047676 A1 | 4/2007 |
| WO | 2007/059871 A1 | 5/2007 |
| WO | 2008/042223 A1 | 4/2008 |
| WO | 2008/098244 A1 | 8/2008 |
| WO | 2009/140342 A1 | 11/2009 |
| WO | 2010/030722 A1 | 3/2010 |
| WO | 2010/039789 A1 | 4/2010 |
| WO | 2010/071750 A1 | 6/2010 |
| WO | 2010/088061 A1 | 8/2010 |
| WO | 2010/098948 A1 | 9/2010 |
| WO | 2010/098994 A1 | 9/2010 |
| WO | 2011/007722 A1 | 1/2011 |
| WO | 2011/119541 A1 | 9/2011 |

OTHER PUBLICATIONS

American Diabetes Association. "Dyslipidemia management in adults with diabetes." Diabetes care 27 Suppl 1 (2004): s68-s71.*

Shen, Dong-Ming, Songnian Lin, and Emma R. Parmee. "A survey of small molecule glucagon receptor antagonists from recent patents (2006-2010)." Expert opinion on therapeutic patents 21.8 (Jun. 2011): 1211-1240.*

Winkler, Karl, et al. "Ezetimibe alone and in combination lowers the concentration of small, dense low-density lipoproteins in type 2 diabetes mellitus." Atherosclerosis 220.1 (Nov. 2011): 189-193.*

Bangalore, Sripal, et al. "Fixed-dose combinations improve medication compliance: a meta-analysis." The American journal of medicine 120.8 (2007): 713-719.*

Kumar, Kotta Kranthi, M. Mahesh, and K. Sasikanth. "Design, Development and characterization of sustained release of Metformin and Gliclazide bi-layered tablets." International Journal of Biopharmaceutics 1.2 (2010): 67-71.*

Parmee, et al., "Discovery of MK-0893: A glucagon receptor antagonist for the treatment of type II diabetes", 241st ACS National Meeting & Exposition, Mar. 27-31, 2011, MEDI-31.

American Diabetes Association, "Diagnosis and Classification of Diabetes Mellitus", Diabetes Care, vol. 35, Supp. 1, S64-S71 (2012).

Burnett, etal., "2-Azetidinones as lnhibitorss of Cholesterol Absorption", J. of Medicinal Chemistry, vol. 37, No. 12, pp. 1733-1736 (1994).

Byers, et al., "Further Studies Concerning Glucagon-Induced Hypocholesterolemia", Society for Experimental Biology and Medicine, vol. 149, pp. 151-157 (1975).

DeLaszlo, et al., "Potent, Orally Absorbed Glucagon Receptor Antagonists", Biorganic & Medicinal Chemistry Letters,vol. 9, pp. 641-646 (1999).

Eldor, et al., "Is there evidence?", Diabetes Care, vol. 32, Supp. 2, S384-S391.

American Diabetes Association, "Standards of Medical Care in Diabetes—2021", Diabetes Care, vol. 35, Supp. 1, pp. S11-S63 (2012).

Dujovne, et al., "Reduction of LDL Cholesterol in Patients with Primary Hypercholesterolemia by SCH 48461: Results of a Multi-center Dose-Ranging Study", J. Clin. Pharmacology, vol. 41, pp. 70-78 (2001).

Dujovne, et al., "Efficacy and Safety of a Potent New Selective Cholesterol Absorption Inhibitor, Ezetimibe, in Patients with Primary Hypercholesterolemia", Amer. J. Cardiol., vol. 90, pp. 1092-1097 (2002).

Edwards, et al., "The effect of glucagon, norepinephrine, and dibutyryl cyclic AMP on cholesterol efflux and on the activity of 3-hydroxy-3-methylglutaryl CoA reductase in rat hepatocytes", Journal of Lipid Research, vol. 20, pp. 2-7 (1979).

Engel, et al., "Efficacy and safety of the glucagon receptor antagonist, MK-0893, in combination with metformin or sitagliptin in patients with type 2 diabetes mellitus", EASD 2011 Presentation 191.

Engel, et al., Efficacy and Tolerability of MK-0893, a glucagon receptor antagonist (GRA), in patients with type 2 diabetes (T2DM), ADA Abstract No. 309-0R.

Engel, et al., "Glycemic and Lipid Effects of the Short-Acting Glucagon Receptor Antagonist MK-3577 in Patients with Type 2 Diabetes", 72nd Scientific Sessions of the American Diabetes Association. Philadelphia, PA (Jun. 12, 2012) Diabetes, vol. 61, Supp. 1, pp. A266 (2012).

Goodman, et al., "Hormonal regulation of canine intestinal cholesterol synthesis", Am. J. Physiol., vol. 240(4), pp. G274-G280 (1981).

Guettet, et al., Effects of chronic glucagon administration on cholesterol and bile acid metabolism, Biochimica et Biophysica Acta, vol. 963, pp. 215-223 (1988).

Guettet, et al., "Effect of Chronic Glucagon Administration on Lipoprotein Composition in Normally Fed, Fasted and Cholesterol-Fed Rats", Lipids, vol. 26, pp. 451-458 (1991).

Howles, et al., "Cholesterol absorption and metabolism", Methods in Molecular Biology, vol. 602, pp. 157-179 (2010).

Ingebritsen, et al., Modulation of Hydroxymethylglutaryl-CoA reductase activity, reductase kinase activity, and cholesterol synthesis in rat hepatocytes in response to insulin and glucagon, Journal of Biological Chemistry, vol. 254, No. 20, pp. 9986-9989 (1979).

Ingebritsen, et al., Protein phosphorylation and the hormonal control of hepatic cholesterol synthesis, Biochemical Society Transactions, vol. 11, No. 6, pp. 644-646 (1983).

Jaya, et al., "Mechanism of hypocholesterolemic action of glucagon", J. Bioscience, vol. 12, No. 2, pp. 111-114 (1987).

MacKay et al., "Evaluation of methods for the determination of cholesterol absorption and synthesis in humans", Atherosclerosis, vol. 218, pp. 253-262 (2011).

Nesto, "LDL Cholesterol lowering in type 2 diabetes: What is the optimum approach?", Clinical Diabetes, vol. 26, No. 1, pp. 8-13 (2008).

Pullinger, et al., "Effects of hormones and pyruvate on the rates of secetion of very-low-density lipoprotein triacylglycerol and cholesterol by rat hepatocytes", Biochimica et Biophysica Acta, vol. 833, pp. 44-51 (1985).

Quintao, et al., "An evaluation of four methods for measuring cholesterol absorption by the intestine in man", Journal of Lipid Research, vol. 12, pp. 221-232 (1971).

Rothfeld, et al.M "Effects of Glucagon on Cholesterol and Triglyceride Deposition in Tissues", Biochemical Medicine, vol. 10, pp. 122-125 (1974).

Ruddy, et al., Inhibition of Glucagon-Induced Hyperglycemia Predicts Glucose Lowering Efficacy of a Glucagon Receptor Antagonist, MK-0893, in Type 2 Diabetes (T2DM), American Diabetes Association, Abstract 311-OR (Jun. 2011).

Salisbury, et al. Hypocholesterolemic activity of a novel inhibitor of cholesterol absorption, SCH 48461, Atherosclerosis, vol. 115, pp. 45-63 (1995).

Xiong, et al., Discovery of a Novel Glucagon Receptor Antagonist . . . , Journal of Medicinal Chemistry, vol. 55, pp. 6137-6148 (2012).

Yoshikawa, et al., "Catalytic Enantioselective Hydrogenation of N-Alkoxycarbonyl Hydrazones: A Practical Synthesis of Chiral Hydrazines", Organic Letters, vol. 12, No. 2, pp. 276-279 (2010).

Berthet, J., "The Influence of Glucagon and Adrenaline on the In Vitro Synthesis of Cholesterol by Liver Tissue", Radioisotopes Sci. Research, vol. 111, pp. 179-182 (1958) Google Translation: French to English.

Jankovic, et. al., "Glucagon and Lipid Metabolism", Acta Med. Medianae, vol. 11, No. 6, pp. 34-38 (1972) Google Translation: Bosnian/Croatian to English.

Smietanska, et al., "Effect of Glucagon on Cholesterol and Lipid Biosynthesis in Rat Liver", Pol. Arch. Med. Wewn., vol. 39, No. 7, pp. 67-71 (1967) Google Translation: Polish to English.

Butturini, et al., "Action of Elastase and of Glucagon on Cholesterolemia", Bollettino—Societa Italiana de Biologia Sperimentale, vol. 35, pp. 27-29 (1959) Google Translation: Italian to English.

(56) References Cited

OTHER PUBLICATIONS

Butturini, et al., "Action of Glucagon on the Arteriopathy of a Hypercholesterol diet in the Rabbit", Bollettino—Societa Italiana de Biologia Sperimentale, vol. 34, pp. 14-16 (1958) Google Translation: Italian to English.
International Search Report of PCT/US2013/073780, dated Mar. 2, 2014.
Written Opinion of PCT/US2013/073780, dated Mar. 2, 2014.
Caren, et al., "Glucagon and Cholesterol Metabolism", Metabolism, Clinical and Experimental, vol. 9, pp. 938-945 (1960).
Friedman, et al., "Effect of Glucagon on Blood Cholesterol Levels in Rats", Lancet, vol. 2, pp. 464-466 (1971).
Wang, et al., "Measurement of intestinal cholesterol absorption by plasma and fecal dual-isotope ratio, mass balance, and lymph fistula methods in the mouse: an analysis of direct versus indirect methodologies", Journal of Lipid Research, vol. 44, pp. 1042-1059 (2003).
Malinovska, et al., "Effect of a single dose of glucagon on some lipid parameters in healthy subjects", Vnitrni Lekarstvi, vol. 29, pp. 961-968 (1983) Google Translation: Czech to English.
Nesto et al., Beyond Low-Density Lipoprotein, Am J Cardiovasc Drugs, 2005, 379-387, 5(6).

* cited by examiner

METHODS OF TREATING DIABETES BY ADMINISTERING A GLUCAGON RECEPTOR ANTAGONIST IN COMBINATION WITH A CHOLESTEROL ABSORPTION INHIBITOR

CROSS-REFERENCE TO RELATED APPLICATIONS

This application is a continuation of application Ser. No. 14/649,651, filed Jun. 4, 2015, which is a U.S. National Phase application under 35 U.S.C. § 371 of PCT/US13/073780, filed Dec. 8, 2013, and claims priority from and the benefit of U.S. Provisional Application No. 61/735,304, filed Dec. 10, 2012.

BACKGROUND OF THE INVENTION

Diabetes refers to a disease process derived from multiple causative factors and is characterized by elevated levels of plasma glucose (hyperglycemia) in the fasting or postprandial state. Elevated levels of plasma glucose can result in various symptoms, including impacted (blurry) vision, excessive thirst, fatigue, hunger, frequent urination and weight loss. Left untreated, hyperglycemia can lead to serious vision problems, sores and infections in the feet and skin, nerve damage, and cardiovascular complications.

Absolute or relative elevations in glucagon levels have been shown to contribute to the hyperglycemic state in some patients with type 1 or type 2 diabetes. Glucagon is a key hormonal agent that acts in concert with insulin to mediate homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Glucagon exerts its action by binding to and activating its receptor. Both in healthy control animals as well as in animal models of type 1 and type 2 diabetes, neutralization of the effect of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon action could be a useful adjunct to conventional treatment of hyperglycemia in diabetic patients. The action of glucagon can be suppressed by providing an antagonist or an inverse agonist, e.g., substances that inhibit or prevent constitutive, or glucagon-induced, glucagon receptor-mediated responses.

While diabetic patients frequently exhibit poor blood-lipid profiles with high levels of LDL cholesterol and low levels of HDL cholesterol, there are a significant number of diabetic and pre-diabetic patients that do not possess these cardiovascular risk factors. Understanding and ensuring effective and appropriate treatment of diabetes in this patient population that may not be exhibiting the typical cardiovascular disease risk factors is a significant goal.

SUMMARY OF THE INVENTION

The present invention relates to a method of treating diabetes or reducing hyperglycemia in a subject having an LDL cholesterol plasma level of less than 130 mg/dL by administering a glucagon receptor antagonist in combination with a cholesterol absorption inhibitor.

BRIEF DESCRIPTION OF THE DRAWINGS

FIG. 14A), 40 mg (n=42, FIG. 14B), 60 mg (n=46, FIG. 14C) and 80 mg (n=42; FIG. 14D).

DETAILED DESCRIPTION OF THE INVENTION

Figure 1:
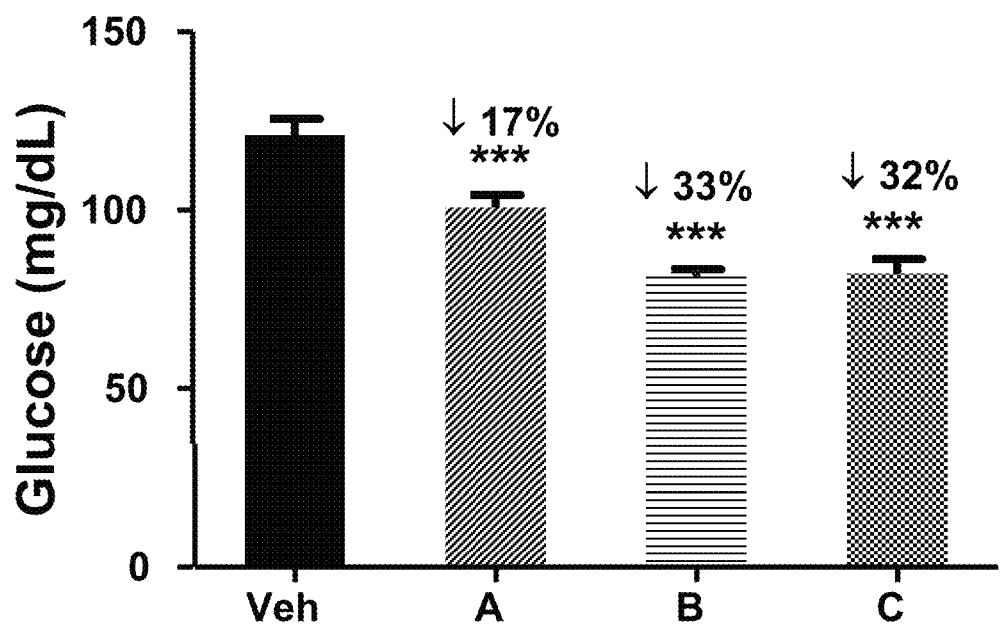
FIG. 1 illustrates plasma glucose in hGCGR mice following sub-chronic treatment with vehicle or GRA compounds A, B or C at 30 mpk QD for 5 days (n=8).

The present invention relates to a method of treating diabetes or reducing hyperglycemia in a subject in need thereof having an LDL cholesterol plasma level of less than 130 mg/dL by administering a glucagon receptor antagonist in combination with a cholesterol absorption inhibitor.

The present invention further relates to a method for treating one or more of the following conditions in a subject in need thereof having an LDL cholesterol plasma level of less than 130 mg/dL: (1) hyperglycemia, (2) low glucose tolerance, (3) insulin resistance, (4) retinopathy, (5) nephropathy, (6) neuropathy, (7) Syndrome X and (8) other conditions and disorders where insulin resistance is a component; which comprises administering a glucagon receptor antagonist in combination with a cholesterol absorption inhibitor to a subject having an LDL cholesterol plasma level of less than 130 mg/dL. An individual having the one or more conditions above along with diabetes or pre-diabetes is considered a subject in need thereof.

The present invention further relates to a method for preventing one or more of the following conditions in a subject in need thereof having an LDL cholesterol plasma level of less than 130 mg/dL: (1) lipid disorders, (2) dyslipidemia, (3) hyperlipidemia, (4) hypertriglyceridemia, (5) hypercholesterolemia, (6) low HDL levels, (7) high LDL levels, (8) atherosclerosis and its sequelae and (9) vascular restenosis; which comprises administering a glucagon receptor antagonist in combination with a cholesterol absorption inhibitor to a subject having an LDL cholesterol plasma level of less than 130 mg/dL. An individual having diabetes or pre-diabetes is considered a subject in need thereof.

In particular embodiments of the methods and compositions of the present invention, the subject has an LDL cholesterol plasma level of less than 120 mg/dL, less than 110 mg/dL, less than 100 mg/dL or less than 75 mg/dL.

In particular embodiments of the methods and compositions of the present invention, the subject is further not being treated with a statin.

As used herein "treating diabetes" and alternate versions thereof such as "treatment of diabetes" means the treatment of the condition characterized as diabetes in a subject, or addressing the symptoms thereof in the subject. Throughout the present application, the terms patient, individual and subject will be used interchangeably and mean the same thing—an individual receiving the combination described herein.

"Diabetes" includes four clinical classes as set forth in the Standards of Medical Care in Diabetes, 2012, 2012 *Diabetes Care* 35(Supp. 1): S11-S63: (1) Type 1 diabetes resulting from β-cell destruction; (2) Type 2 diabetes resulting from a progressive insulin secretory defect, (3) other specific types of diabetes; and (4) gestational diabetes mellitus ("GDM"): The present invention specifically encompasses the treatment of each one of these conditions individually and an individual having any one of these conditions is considered a subject in need of treatment for diabetes. Diabetic individuals are typically characterized as having one, two or more of the following conditions: (a) fasting plasma glucose greater than or equal to 126 mg/dt; (b) 2 hour plasma glucose greater than or equal to 200 mg/dL, in a 75 gram oral glucose tolerance test ("OGTT"; see American Diabetes Association, 2012 (Suppl. 1): S64-S71); or (c) HbA1c greater than or equal to 6.5%. These characterizations are readily known and understood by those of skill in the art; see Standards of Medical Care in Diabetes, supra. HbA1c or A1c (used interchangeably herein) refers to a form of glycated or glycosylated hemoglobin used as a surrogate marker for blood glucose levels.

To diagnose GDM, a 75-g OGTT, with plasma glucose measurements at fasting, 1 hour and 2 hour is performed at 24-48 weeks' gestation in women not previously diagnosed with overt diabetes; see Standards of Medical Care in Diabetes, supra. Individuals with GDM are typically characterized as having one, two or more of the following conditions: (a) fasting plasma glucose greater than or equal to 92 mg/dL; (b) 1 hour plasma glucose greater than or equal to 180 mg/dL in a 75 grain OGTT; or (c) 2 hour plasma glucose of greater than or equal to 153 mg/dL in a 75 gram OGTT; supra.

Treatment of diabetic patients as contemplated herein should bring down one or more of the following: (i) fasting plasma glucose, (ii) postprandial glucose, and (iii) HbA1c, thus ameliorating the diabetic condition and working to prevent acute complications and reduce the risk of long-term complications. For instance, as noted in the Standards of Medical Care in Diabetes, supra, lowering A1C in a diabetic patient to below or around 7% has been shown to "reduce microvascular complications of diabetes, and if implemented soon after the diagnosis of diabetes is associated with long-term reduction of microvascular disease." Depending on the particular patient and their condition, the individual goal may be more strict (e.g., less than 6.5%) or more lenient (e.g., less than 8%). It will depend on the physician's prognosis and treatment plan. In specific embodiments of the present invention, treatment results in a reduction in A1c by at least 0.5%. In additional individual embodiments, treatment results in a reduction in A1c by at least 1%, 1.5%, 2.0%, 2.5%, 3.0%, 3.5%, or more.

"Reducing hyperglycemia" as used herein means effectuating a reduction in A1c in the patient. In specific embodiments, treatment results in a reduction in A1c by at least 0.1 In additional individual embodiments, treatment results in a reduction in A1c by at least 0.5%, 1%, 1.5%, 2.0%, 2.5%, 3.0%, 3.5%, or more. In general, the A1c measurement reflects a person's average blood glucose levels for the past 3 months. A 1% change in A1c equates to a change of approximately 35 mg/dL in average blood glucose. Commercial means for measuring A1c have been available since the late 1970s and the significance thereof in terms of diagnosing diabetes is well understood by those of skill in the art; see, e.g., Standards of Medical Care in Diabetes, supra. In addition to being effective in the treatment of diabetic patients, reducing hyperglycemia provides a therapeutic advantage to those individuals at heightened risk of developing diabetes, herein pre-diabetic patients. In one embodiment, the present invention is directed to the reduction of hyperglycemia in pre-diabetic patients. Pre-diabetic individuals are typically characterized as having one, two or more of the following conditions: (a) a fasting plasma glucose in the range of 100 mg/dL and 125 mg/dL; (b) 2 hour plasma glucose in the range of 140 mg/dL and 199 mg/dL in a 75 grain OGTT; or (c) HbA1c in the range of 5.7% and 6.4%. An individual having diabetes or pre-diabetes is considered a subject in need of treatment for reducing hyperglycemia.

In specific embodiments of the present invention, prior to administration of the combination of glucagon receptor antagonist and cholesterol absorption inhibitor, the levels of cholesterol absorption are measured. Means for measuring cholesterol absorption are well known in the art; see, e.g., Wang and Carey, 2003 *J. Lipid Res.* 44:1042-1059; Howles, 2010 *Methods Mol Biol* 602; 157-179; Mackay & Jones, 2011 *Atherosclerosis* 218(2): 253-262; and Quintao et al., 1971 *J. Lip. Res.* 12:221-232. In specific embodiments, the levels of cholesterol absorption are measured using a cholesterol absorption biomarker. In specific embodiments, thereof, the cholesterol absorption biomarker is sitosterol, campesterol or cholestanol.

A "glucagon receptor antagonist" is defined herein as a compound able to bind to the glucagon receptor and thereby antagonize the activity of glucagon mediated by the glucagon receptor. Inhibiting the activity of glucagon by antagonizing the binding and activity of glucagon at the glucagon receptor reduces the rate of gluconeogenesis and glycogenolysis, and the concentration of glucose in plasma. Methods by which to determine the binding of a supposed antagonist with the glucagon receptor are known in the art and means by which to determine the interference with glucagon activity at the glucagon receptor are publicly available; see, e.g., S. E. de Laszlo et at., 1999 *Bioorg. Med. Chem. Lett.* 9:641-646. The present invention is particularly directed to glucagon receptor antagonists having as a functional component thereof a small molecule compound, or in other words a low molecular weight organic compound. A small molecule is typically less than 800 Daltons.

The glucagon receptor antagonist in specific individual embodiments is selected from one of the following patent publication disclosures: WO 07/47676; WO 06/86488; WO 05/123688; WO 05/121097; WO 06/14618; WO 08/42223; WO 08/98244; WO 2010/98948; US 20110306624; WO 2010/98994; WO 2010/88061; WO 2010/71750; WO 2010/30722; WO 06/104826; WO 05/65680; WO 06/102067; WO 06/17055; WO 2011/07722; or WO 09/140342; although by no means limited hereto.

In particular embodiments of the invention described herein, the glucagon receptor antagonist compound is one of the following compounds:

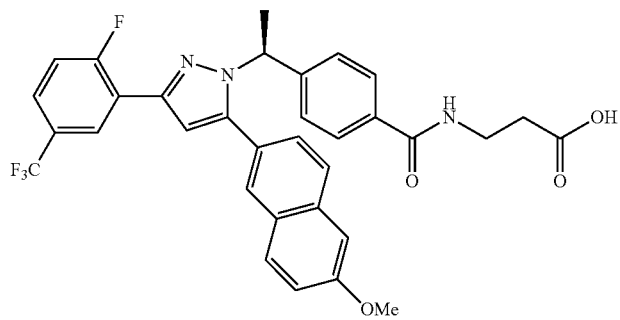 [SMILES: COc1ccc2cc(-c3cc(-c4cc(C(F)(F)F)ccc4F)nn3[C@@H](C)c3ccc(C(=O)NCCC(=O)O)cc3)ccc2c1]

Compound A

N-[4-[(1S)-1-[3-2-fluoro-5-(trifluoromethyl)phenyl]-5-(6-methoxy-2-naphthalenyl)-1H-pyrazol-1-yl]ethyl]benzoyl]-β-alanine;
the structure and/or general synthesis of which is described in U.S. Pat. No. 7,598,285 (see, e.g., Ex. 5),

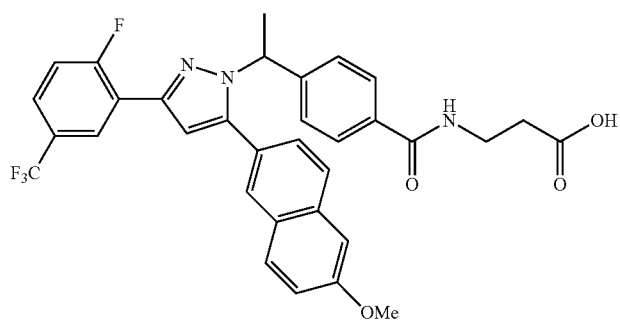 [SMILES: COc1ccc2cc(-c3cc(-c4cc(C(F)(F)F)ccc4F)nn3C(C)c3ccc(C(=O)NCCC(=O)O)cc3)ccc2c1]

Compound A-I 3-(4-(1-(3-(2-fluoro-5-(trifluoromethyl)phenyl)-5-(6-methoxynaphthalen-2-yl)-1H-pyrazol-1-yl)ethyl)benzamido)propanoic acid;
the structure and/or general synthesis of which is described in U.S. Pat. No. 7,598,285,

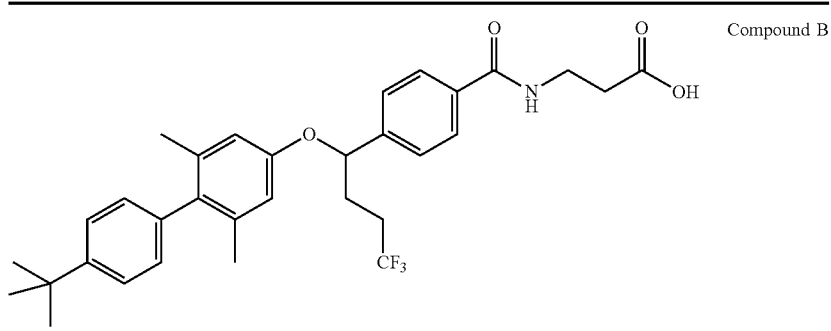

Compound B

3-{4-[1-(4'-tert-butyl-2,6-dimethyl-biphenyl-4-yloxy)-4,4,4-trifluoro-butyl]-benzoylamino}-propionic acid;
the structure and/or general synthesis of which is described in U.S. Pat. No. 7,816,557 (see, e.g., Exs. 393-394),

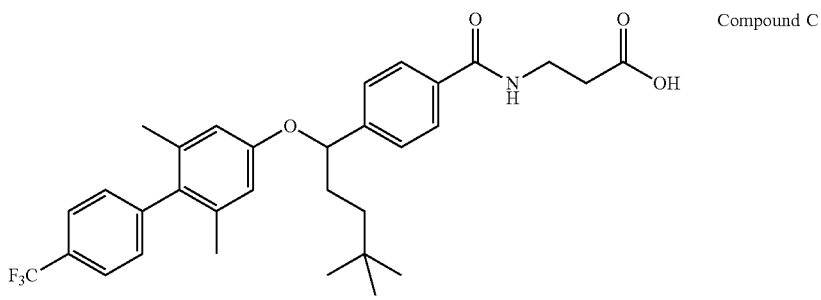

Compound C

3-{4-[1-(2,6-Dimethyl-4'-trifluoromethyl-biphenyl-4-yloxy)-4,4-dimethyl-pentyl]-benzoylamino}-propionic acid;
the structure and/or general synthesis of which is described in U.S. Pat. No. 7,816,557 (see, e.g., Ex. 325),

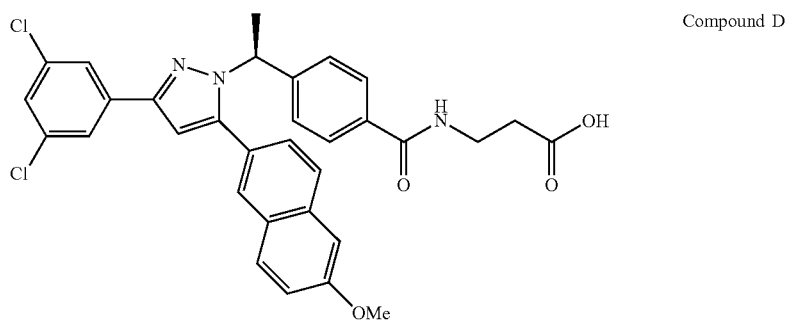

Compound D

N-(4-{(1S)-1-[3-(3,5-dichlorophenyl)-5-(6-methoxy-2-naphthyl)-1H-pyrazol-1-yl]ethyl}benzoyl)-β-alanine;
the structure and/or general synthesis of which is described in Xiong et al., 2012 J. Med. Chem. 55(13):6138-6148; and U.S. Pat. No. U.S. 7,598,285 (see, e.g., Ex. 4),

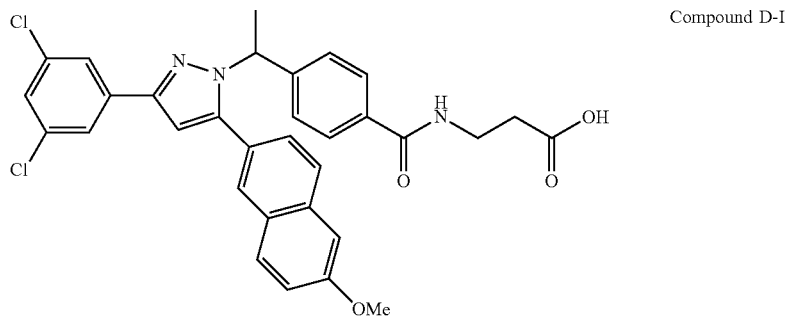

Compound D-I 3-(4-(1-(3-(3,5-dichlorophenyl)-5-(6-
methoxynaphthalen-2-yl)-1H-pyrazol-1-
yl)ethyl)benzamido)propanoic acid;
the structure and/or general synthesis of which is
described in Xiong et al., 2012 J. Med. Chem.
55(13):6138-6148; and U.S. Pat. No.
U.S. 7,598,285,

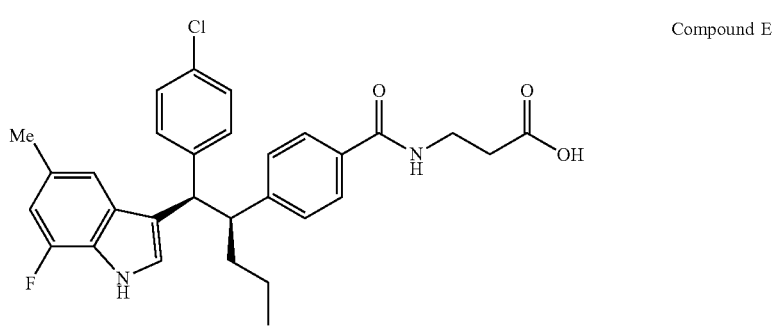

Compound E

N-(4-{(1S)-1-[(R)-(4-chlorophenyl)(7-fluoro-5-
methyl-1H-indol-3-yl)methyl]butyl}benzoyl)-β-
alanine;
the structure and/or general synthesis of which is
described in U.S. Pat. No. 7,687,534, see, e.g.,
Ex. 2,

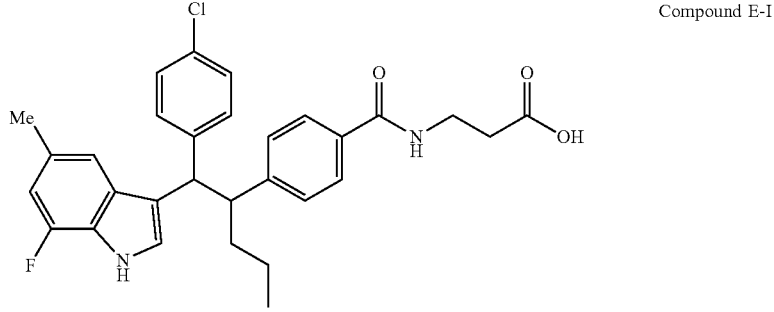

Compound E-I 3-(4-(1-(4-chlorophenyl)-1-(7-fluoro-5-methyl-
1H-indol-3-yl)pentan-2-yl)benzamido)propanoic
acid;
the structure and/or general synthesis of which is
described in U.S. Pat. No. 7,687,534,

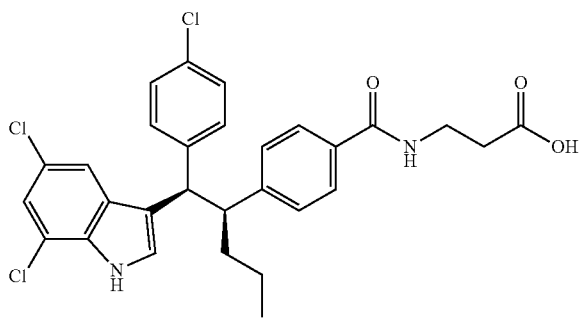 [SMILES: CCC[C@H](c1ccc(C(=O)NCCC(=O)O)cc1)[C@H](c1ccc(Cl)cc1)c1c[nH]c2c(Cl)cc(Cl)cc12]

Compound F

N-[4-[(1S)-1-[®-(4-chlorophenyl)(5,7-dichloro-
1H-indol-3-yl)methyl]butyl]benzoyl]-β-alanine
the structure and/or general synthesis of which is
described in U.S. Pat. No. 7,687,534; see, e.g.,
Ex. 1,

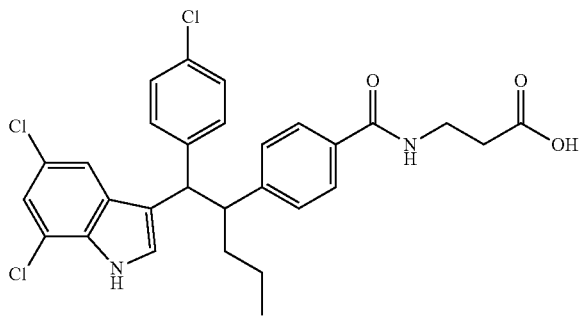 [SMILES: CCCC(c1ccc(C(=O)NCCC(=O)O)cc1)C(c1ccc(Cl)cc1)c1c[nH]c2c(Cl)cc(Cl)cc12]

Compound F-I 3-(4-(1-(4-chlorophenyl)-1-(5,7-dichloro-1H-
indol-3-yl)pentan-2-yl)benzamido)propanoic
acid;
the structure and/or general synthesis of which is
described in U.S. Pat. No. 7,687,534,

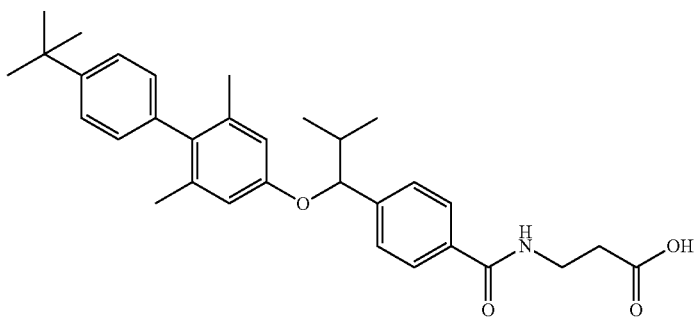 [SMILES: Cc1cc(OC(c2ccc(C(=O)NCCC(=O)O)cc2)C(C)C)cc(C)c1-c1ccc(C(C)(C)C)cc1]

Compound G

3-{4-[1-(4'-tert-Butyl-2,6-dimethyl-biphenyl-4-
yloxy)-2-methyl-propyl]-benzoylamino}-
propionic acid;
the structure and/or general synthesis of which is
described in U.S. Pat. No. 7,816,557, see, e.g.,
Exs. 202-203,

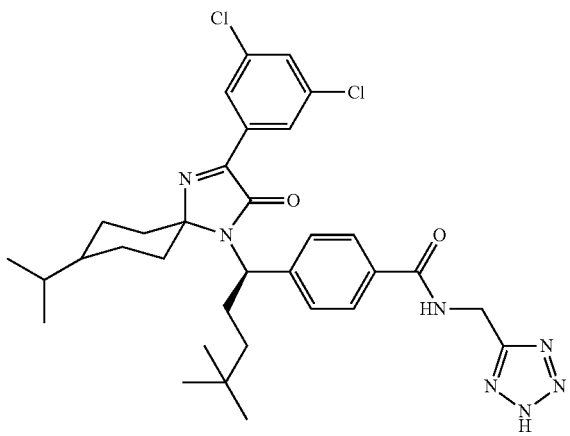 [SMILES: CC(C)C1CCC2(CC1)N=C(c1cc(Cl)cc(Cl)c1)C(=O)N2[C@H](CCC(C)(C)C)c1ccc(C(=O)NCc2nn[nH]n2)cc1]

Compound H

N-((2H-tetrazol-5-yl)methyl)-4-((1R)-1-(8-(tert-butyl)-3-(3,5-dichlorophenyl)-2-oxo-1,4-diazaspiro[4.5]dec-3-en-1-yl)-4,4-dimethylpentyl)benzamide;
the structure and/or general synthesis of which is described in WO 2010/039789, see, e.g., Ex. 1.45,

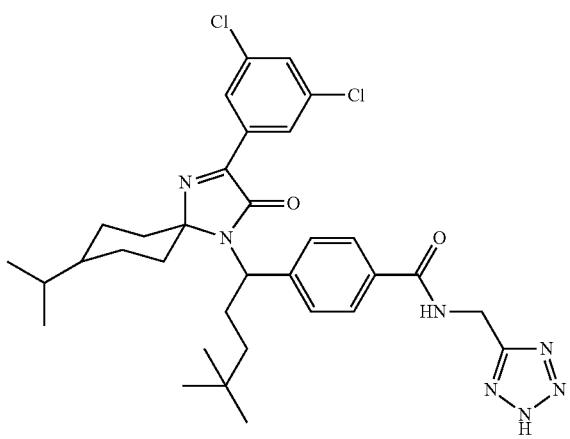 [SMILES: CC(C)C1CCC2(CC1)N=C(c1cc(Cl)cc(Cl)c1)C(=O)N2C(CCC(C)(C)C)c1ccc(C(=O)NCc2nn[nH]n2)cc1]

Compound H-I

N-((2H-tetrazol-5-yl)methyl)-4-(1-(8-(tert-butyl)-3-(3,5-dichlorophenyl)-2-oxo-1,4-diazaspiro[4.5]dec-3-en-1-yl)-4,4-dimethylpentyl)benzamide;
the structure and/or general synthesis of which is described in WO 2010/039789,

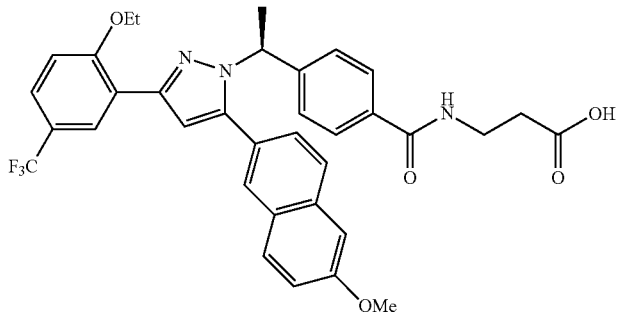 [SMILES: CCOc1ccc(C(F)(F)F)cc1-c1cc(-c2ccc3cc(OC)ccc3c2)n([C@@H](C)c2ccc(C(=O)NCCC(=O)O)cc2)n1]

Compound I (S)-3-(4-(1-(3-(2-ethoxy-5-
(trifluoromethyl)phenyl)-5-(6-
methoxynaphthalen-2-yl)-1H-pyrazol-1-
yl)ethyl)benzamido)propanoic acid;
the structure and/or general synthesis of which is
described in U.S. Publication No.
US20070088070, see, e.g., Ex. 10,

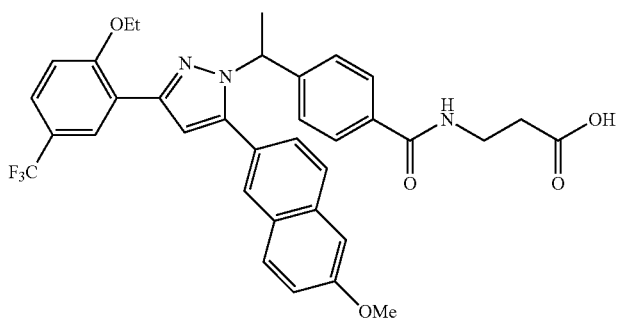

Compound I-I 3-(4-(1-(3-(2-ethoxy-5-(trifluoromethyl)phenyl)-5-
(6-methoxynaphthalen-2-yl)-1H-pyrazol-1-
yl)ethyl)benzamido)propanoic acid;
the structure and/or general synthesis of which is
described in U.S. Publication No.
US20070088070,

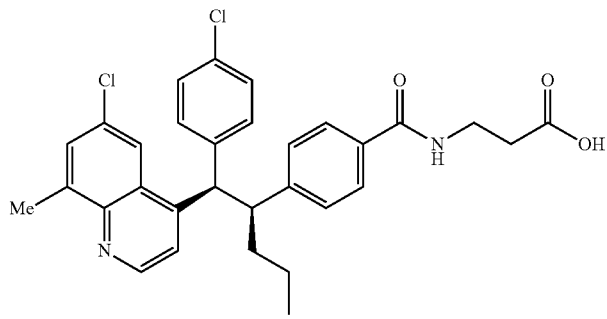 [SMILES: CCC[C@H](c1ccc(C(=O)NCCC(=O)O)cc1)[C@H](c1ccc(Cl)cc1)c1ccnc2c(C)cc(Cl)cc12]

Compound J 3-(4-((1R,2S)-1-(6-chloro-8-methylquinolin-4-
yl)-1-(4-chlorophenyl)pentan-2-
yl)benzamido)propanoic acid;
the structure and/or general synthesis of which is
described in WO 2010/30722, see, e.g., Ex. 1,

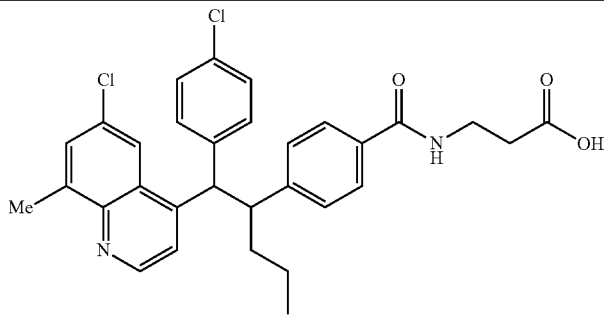

Compound J-I 3-(4-(1-(6-chloro-8-methylquinolin-4-yl)-1-(4-chlorophenyl)pentan-2-yl)benzamido)propanoic acid;
the structure and/or synthesis of which is described in WO 2010/30722, or a pharmaceutically acceptable salt thereof.

According to this invention, it is to be understood that the definitions of the above listed glucagon receptor antagonists also comprise their pharmaceutically acceptable salts as well as all hydrates, solvates and polymorphic forms thereof as individual embodiments hereof.

A "cholesterol absorption inhibitor" is defined herein as a compound able to prevent or reduce the uptake of cholesterol from the small intestine into the circulatory system. Cholesterol absorption inhibitors are effective in lowering the levels of total cholesterol and LDL cholesterol. The measurement of lipids is well known in the art including upon treatment with cholesterol absorption inhibitors, see, e.g., Dujovne et al., 2002 Am. J. Cardiol. 90(10): 1092-1097. The present invention is particularly directed to cholesterol absorption inhibitors having as a functional component thereof a small molecule compound, or in other words a low molecular weight organic compound. A small molecule is typically less than 800 Daltons.

The cholesterol absorption inhibitor in specific individual embodiments is selected from one of the following patent or scientific journal publication disclosures: U.S. Pat. No. RE 42,461; WO 07/59871; WO 07/47676; WO 06/86488; WO 05/123688; WO 05/121097; WO 06/14618; WO 08/42223; WO 08/98244; WO 2010/98948; US 20110306624; WO 2010/98994; WO 2010/88061; WO 2010/71750; WO 2010/30722; WO 06/104826; WO 05/65680; WO 06/102067; WO 06/17055; WO 2011/07722; WO 09/140342; or B. G. Salisbury et al., 1995 Atherosclerosis 115:45-63 and Burnett et al., 1994 J. Med. Chem. 137:733; although by no means limited thereto.

In specific embodiments, the cholesterol absorption inhibitor is ezetimibe:

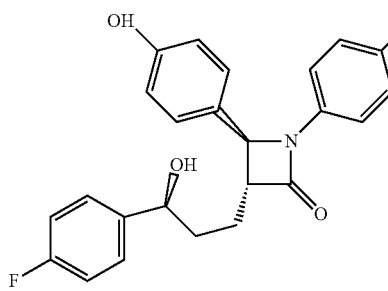

or a pharmaceutically acceptable salt thereof Ezetimibe is described, inter cilia, in U.S. Pat. No. RE 42,461. Ezetiinibe (Zetia®) can be prepared by a variety of methods well known to those skilled in the art, for example such as are disclosed in U.S. Pat. Nos. 5,631,365, 5,767,115, 5,846,966, 6,207,822 and PCT Patent Application WO 93/02048, each of which is incorporated herein by reference In specific embodiments, the cholesterol absorption inhibitor is:

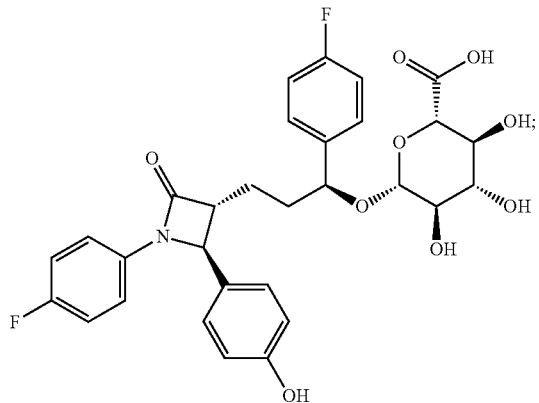 [SMILES: O=C(O)[C@H]1O[C@@H](O[C@@H](CC[C@H]2C(=O)N(c3ccc(F)cc3)[C@@H]2c2ccc(O)cc2)c2ccc(F)cc2)[C@H](O)[C@@H](O)[C@@H]1O]

or a pharmaceutically acceptable salt thereof described, inter aria, in U.S. Pat. No. 6,982,251.

In specific embodiments, the cholesterol absorption inhibitor is:

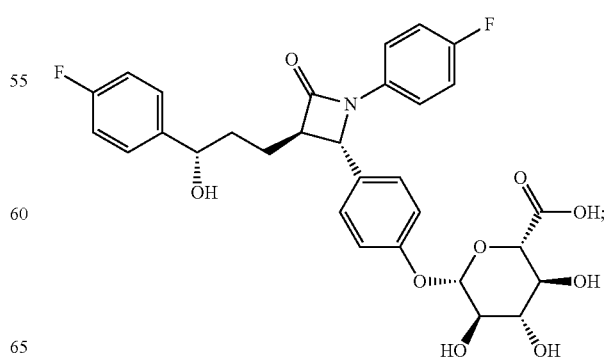

or a pharmaceutically acceptable salt thereof, described, inter alio, in U.S. Pat. No. 5,756,470.

In specific embodiments, the cholesterol absorption inhibitor (SCH-48461) is:

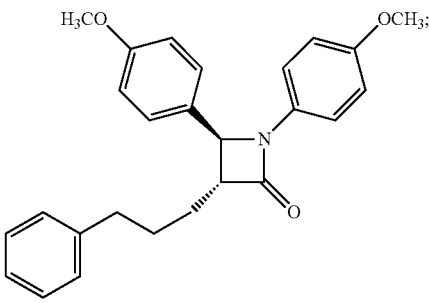 [SMILES: COc1ccc([C@@H]2[C@@H](CCCc3ccccc3)C(=O)N2c2ccc(OC)cc2)cc1]

or a pharmaceutically acceptable salt thereof. SCH-48461 is described, inter alia, in B. G. Salisbury et al., 1995 *Atherosclerosis* 115:45-63, Burnett et al., 1994 *J. Med. Chem.* 137:733, and Dujovne et al., 2001 *J. Clin. Pharmacol.* 41:70-78.

According to this invention, it is to be understood that the definitions of the above listed cholesterol absorption inhibitors also comprise their pharmaceutically acceptable salts as well as hydrates, solvates and polymorphic forms thereof.

The glucagon receptor antagonist and cholesterol absorption inhibitor compounds, in combination, can be used in the manufacture of a medicament for the prophylactic or therapeutic treatment of disease states in mammals associated with elevated levels of glucose, comprised of combining the compounds with a pharmaceutically acceptable carrier to provide the medicament.

Hence, the present invention relates to a combination comprising: (a) a glucagon receptor antagonist, and (b) a cholesterol absorption inhibitor; for use in treating diabetes in mammalian subjects having an LDL cholesterol plasma level of less than 130 mg/dL. The present invention further relates to the use of a combination comprising: (a) a glucagon receptor antagonist, and (b) a cholesterol absorption inhibitor; for the manufacture of a medicament for treating diabetes in mammalian subjects having an LDL cholesterol plasma level of less than 130 mg/dL.

The present invention derives from Applicants' finding that glucagon receptor antagonists can advantageously be used in combination with cholesterol absorption inhibitors for treating diabetes or reducing hyperglycemia particularly in individuals having normal to low LDL cholesterol levels. The combination in this particular patient population significantly improves the control of and any consequent increases of LDL cholesterol levels as compared to use of glucagon receptor antagonist alone. This finding opens up new therapeutic possibilities in the treatment and prevention of type 2 diabetes mellitus and related disease conditions.

In use for therapy, the present invention contemplates that the glucagon receptor antagonist and the cholesterol absorption inhibitor are administered in therapeutically effective amounts. A "therapeutically effective amount" is the dose or amount that produces a therapeutic response or desired effect in a subject or group of individuals. The therapeutic response or desired effect for the glucagon receptor antagonist is defined herein as a reduction in A1c in the subject administered the glucagon receptor antagonist. In specific embodiments, the reduction in A1c is by at least 0.1% or greater. In additional embodiments, treatment results in a reduction in A1c by at least 0.5%, 1%, 1.5%, 2.0%, 2.5%, 3.0%, 3.5%, or more. The therapeutic response for the cholesterol absorption inhibitor is defined herein as a reduction in LDL cholesterol or the prevention or control of any increase in LDL associated with taking the glucagon receptor antagonist. In specific embodiments, the therapeutic response is evidenced by a reduction in LDL levels from that prior to treatment with the cholesterol absorption inhibitor. In specific embodiments, the reduction is by 5% or more. In specific embodiments, the reduction is individually by 10%, 15%, 20% or more. In particular embodiments, the therapeutic response is evidenced by the maintenance of an LDL level of less than 130 mg/dL at baseline following administration of the glucagon receptor antagonist simultaneously or sequentially with the cholesterol absorption inhibitor. In additional embodiments, the therapeutic response is evidenced by the effectuation of or maintenance of an LDL level of less than 120 mg/dL, less than 110 mg/dL, less than 100 mg/dL or less than 75 mg/dL following administration of the glucagon receptor antagonist simultaneously or sequentially with the cholesterol absorption inhibitor. Control of any increase is characterized as maintaining LDL levels to within 5-10% of the level prior to administration of the glucagon receptor antagonist or in specific embodiments below the above ranges, following administration of the glucagon receptor antagonist simultaneously or sequentially with the cholesterol absorption inhibitor.

The dose, prophylactic or therapeutic, of the glucagon receptor antagonist and cholesterol absorption inhibitor compounds will, of course, vary with the nature or severity of the condition to be treated, the particular compound selected and its route of administration. It may also vary according to the age, weight and response of the individual patient. In general, the daily dose range for the individual compounds lies within the range of from about 0.001 mg to about 100 mg per kg, in additional embodiments about 0.01 mg to about 50 mg per kg, and in further embodiments 0.1 to 10 mg per kg, in single or divided doses. It may be necessary to use dosages outside of these limits in some cases. A therapeutically effective amount or a therapeutic or prophylactic dose or terms of similar meaning appearing throughout the application addressing the amount of the compound to be used refer to the dosage ranges provided, taking into account any necessary variation outside of these ranges. These amounts can be readily determined by the skilled physician.

Representative dosages of the individual glucagon receptor antagonist and cholesterol absorption inhibitor compounds for adults range from about 0.1 mg to about 1.0 g per day, preferably about 1 mg to about 500 mg, in single or divided doses. Examples of suitable dosages per day include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses.

In particular embodiments, the present invention relates to methods and compositions herein where the dosage of the glucagon receptor antagonist lies within the range of from about 0.001 mg to about 100 mg per kg, in additional embodiments about 0.01 mg to about 50 mg per kg, and in further embodiments 0.1 to 10 mg per kg, in single or divided doses. In particular embodiments, the dosage is in a range of 0.1 mg per kg to 5 mg per kg. In particular embodiments, the dosage of glucagon receptor antagonist is below 0.1 mg per kg. In particular embodiments, the present invention relates to methods and compositions herein where the dosage of glucagon receptor antagonist is any amount in the range of 10-120 mg per day. In specific embodiments, the dosage of glucagon receptor antagonist is 10, 20 mg, 40 mg, 60 mg, 80, 100 mg or 120 mg per day. In specific individual embodiments, the dosage is 10 mg, 20 mg, 40 mg, 60 mg, 80 mg, 100 mg or 120 mg per day and the glucagon receptor antagonist is Compound D. In specific embodiments, the dosage of glucagon receptor antagonist is any amount in the range of 1-100 mg per day.

In more specific embodiments, the dosage of glucagon receptor antagonist is any amount in the range of 6-50 mg per day. In specific embodiments, the dosage is any amount in the range of 6-50 mg per day and the glucagon receptor antagonist is Compound E.

In particular embodiments, the present invention relates to methods and compositions herein where the dosage of cholesterol absorption inhibitor is 10 mg.

In particular embodiments, the present invention relates to methods and compositions herein where (a) the dosage of glucagon receptor antagonist is (i) in a range of 0.1 mg per kg to 2 mg per kg; (ii) below 0.1 mg per kg, (iii) in the range of 10-120 mg per day, (iv) 10 mg per day, (v) 20 mg per day, (vi) 40 mg per day, (vii) 60 mg per day, (viii) 80 mg per day, (ix) 100 mg per day, (x) 120 mg per day, (xi) in the range of 1-100 mg per day and/or (xii) in the range of 6-50 mg per day; and (b) the dosage of cholesterol absorption inhibitor is 10 mg.

When intravenous administration is employed, a representative dosage range is from about 0.001 mg to about 100 mg (preferably from 0.01 mg to about 10 mg) per kg of body weight per day of each of the glucagon receptor antagonist and cholesterol absorption inhibitor compounds and, in particular embodiments about 0.1 mg to about 10 mg of the compounds per kg of body weight per day.

The glucagon receptor antagonist and the cholesterol absorption inhibitor compounds are used with one or more pharmaceutically acceptable carriers. In particular embodiments, the glucagon receptor antagonist and cholesterol absorption inhibitor compounds have distinct pharmaceutically acceptable carriers. In specific embodiments, the glucagon receptor antagonist and cholesterol absorption inhibitor compounds have the same pharmaceutically acceptable carrier. Pharmaceutical compositions of use herein comprise a glucagon receptor antagonist, a cholesterol absorption inhibitor and at least one pharmaceutically acceptable carrier. The term "composition" encompasses a product comprising the active and inert ingredient(s), any pharmaceutically acceptable excipients that make up the carrier, as well as any product which results, directly or indirectly, from the combination, complexation or aggregation of any two or more of the ingredients, or from dissociation of one or more of the ingredients, or from other types of reactions or interactions between ingredients. The composition comprises therapeutically effective amounts of both glucagon receptor antagonist and cholesterol absorption inhibitor compounds.

Any suitable route of administration may be employed for providing a mammal, especially a human with an effective dosage of the individual glucagon receptor antagonist and cholesterol absorption inhibitor compounds. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredients (both glucagon receptor antagonist and cholesterol absorption inhibitor compounds) with the carrier components. In general, the compositions are prepared by uniformly and intimately admixing the active ingredients with a liquid or finely divided solid carrier component, and then, if necessary, manipulating the blend into the desired product form. For example, a tablet may be prepared by compression or molding. Compressed tablets may be prepared by compressing free-flowing powder or granules, containing the actives optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The glucagon receptor antagonist and cholesterol absorption inhibitor compounds may be administered, by a route and in an amount commonly used, contemporaneously or sequentially with the other. When the compounds are used contemporaneously, a combination pharmaceutical composition containing both glucagon receptor antagonist and cholesterol absorption inhibitor compounds forms one embodiment hereof. In such an embodiment, the glucagon receptor antagonist and the cholesterol absorption inhibitor are present in a single dosage form. In specific embodiments thereof, the glucagon receptor antagonist and cholesterol absorption inhibitor are in a bilayer tablet.

Alternatively, the glucagon receptor antagonist and the cholesterol absorption inhibitor are present each in a separate dosage form for simultaneous or sequential administration. In specific embodiments, the period of time between administration of the glucagon receptor antagonist and cholesterol absorption inhibitor compounds is in the range from 0 minutes to 12 hours. The administration, contemporaneously or sequentially, may be once, twice, three times or four times daily, per compound or combination.

The weight ratio of the glucagon receptor antagonist and cholesterol absorption inhibitor compounds may be varied within wide limits and depends upon the effective dose of each active ingredient. Generally, a therapeutically effective dose of each will be used. Thus, for example, when a glucagon receptor antagonist is combined with a cholesterol absorption inhibitor the weight ratio of the glucagon receptor antagonist to the cholesterol absorption inhibitor will generally range from about 1000:1 to about 1:1000, preferably about 200:1 to about 1:200.

A pharmaceutical composition which is present as a separate or multiple dosage form, preferably as a kit of parts, is useful in combination therapy to flexibly suit the individual therapeutic needs of the patient.

In specific embodiment, a kit of parts comprises:
(a) a first containment containing a dosage form comprising the glucagon receptor antagonist and at least one pharmaceutically acceptable carrier, and
(b) a second containment containing a dosage form comprising the cholesterol absorption inhibitor and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered contemporaneously or sequentially.

A yet further aspect of the present invention is a manufacture comprising a medicament which comprises a glucagon receptor antagonist according to the present invention and a label or package insert which comprises instructions that the medicament may or is to be administered contemporaneously or sequentially with a medicament comprising a cholesterol absorption inhibitor according to the present invention.

Another further aspect of the present invention is a manufacture comprising a medicament which comprises a cholesterol absorption inhibitor according to the present invention and a label or package insert which comprises instructions that the medicament may or is to be administered contemporaneously or sequentially with a medicament comprising a glucagon receptor antagonist according to the present invention.

Synthesis of the compounds and development and manufacture of pharmaceutical compositions comprising same is well understood in the art.

The following examples are illustrative and provided so that the invention might be more fully understood. They should not be construed as limiting the invention in any way. The following abbreviations may be used in the Examples: B.I.D. (bid or BID) is twice (or 2 times) a day; $D_2O$ is deuterium oxide or heavy water; GRA is a glucagon receptor antagonist; h is hours; i.p. is intraperitoneal; i.v. is intravenous; LDL-c is low density lipoprotein cholesterol; MC is methylcellulose; min is minutes; mpk is mg/kg; p.o. is oral (by mouth); PK is pharmacokinetic properties; QD is once (or 1 time) a day; and WT is wild-type.

EXAMPLE 1

Sub-Chronic Treatment with GRA Increased Plasma Total Cholesterol and Phytosterols in hGCGR Mice Methods Male hGCGR mice (Transgenic Research, 8:295-302, 1999) at ~12 wks of age maintained on chow diet were treated with vehicle and GRA Compounds A, B, and C at 30 mpk QD for 5 days (n=8). On Day 1, mice were administered the compounds followed by glucagon-induced glucose tolerance test. On Day 5, mice were fasted at 7:30 am. After dosing at ~9:00 am, the blood glucose was measured at 2-h post dose with a glucometer; see FIG. 1. At 6-h post dose, the tail blood was collected for PK measurement. Mice were euthanized with $CO_2$, and blood was collected by cardiac puncture. The liver was snap frozen in liquid nitrogen with a freezing clamp and saved in −80° C. Plasma was isolated by centrifuging the blood at 8000 rpm for 5 min. The plasma level of total cholesterol was measured by biochemical assay (Wako Chemicals Inc.). The plasma level of lathosterol and phytosterol was measured by LC/MS. To determine cholesterol synthesis. $D_2O$ was administered i.p. at 20 ml/kg on 24 h prior to takedown of the mice. The level of D2 in plasma water and plasma cholesterol was assayed by GC/MS for cholesterol synthesis. Asterisks denote statistical significance between treatment and vehicle groups.

*$p<0.05$, $p<0.01$, and *$p<0.001$ by ANOVA.

Results

Figure 2:
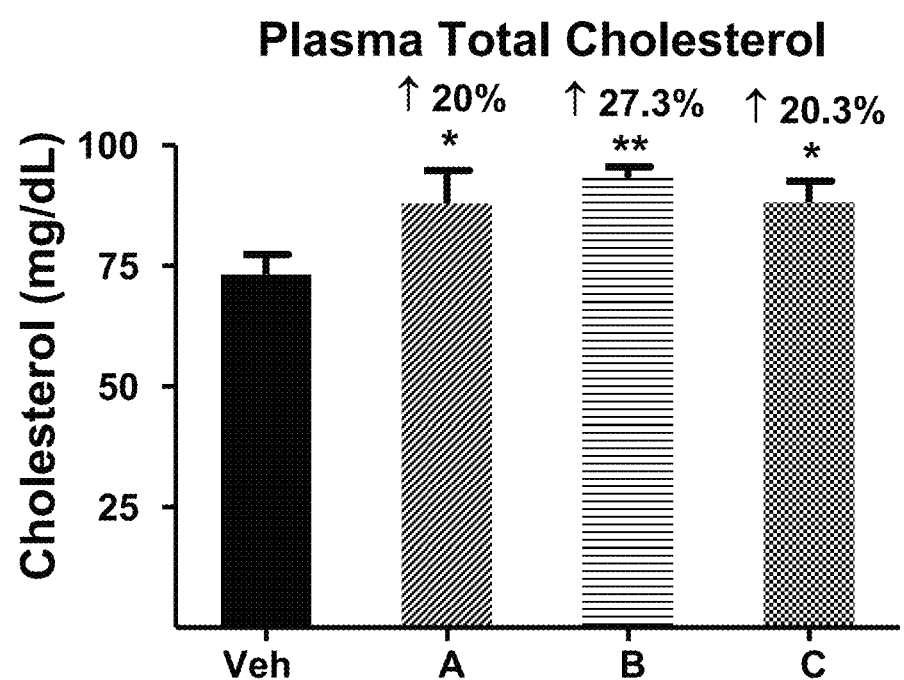
FIG. 2 illustrates plasma total cholesterol in hGCGR mice after sub-chronic treatment with vehicle or GRA Compounds A, B or C at 30 mpk QD for 5 days (n=8).
Figure 3A:
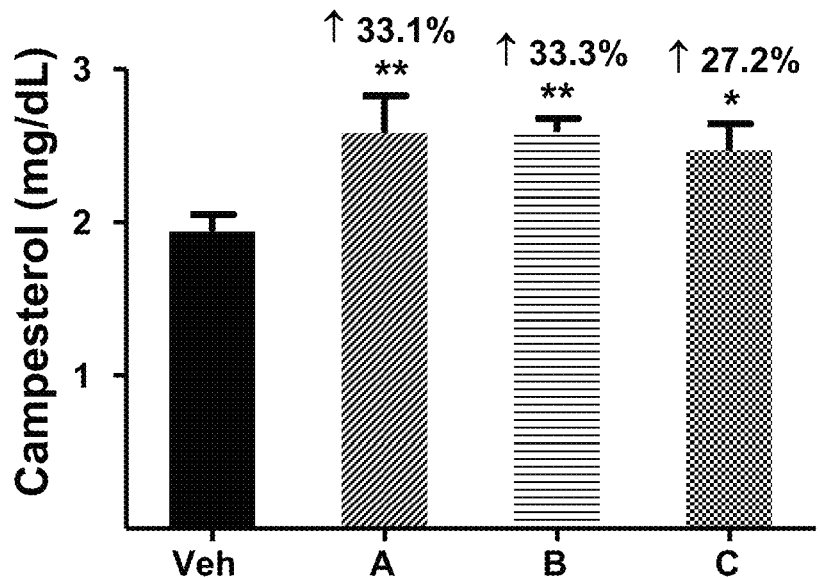
FIGS. 3A-B illustrate plasma levels of phytosterols, campesterol (FIG. 3A) and sitosterol (FIG. 3B) after sub-chronic treatment with vehicle or GRA Compounds A, B or C at 30 mpk QD for 5 days (n=8).
Figure 3B:
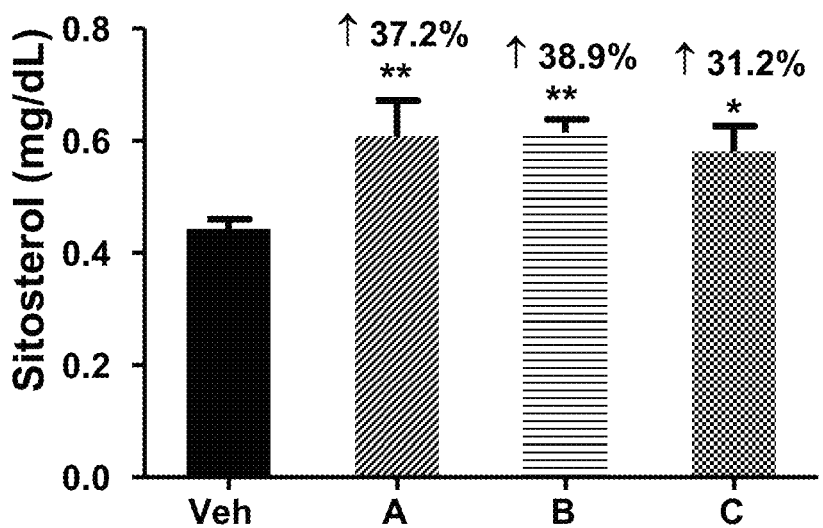
Figure 4A:
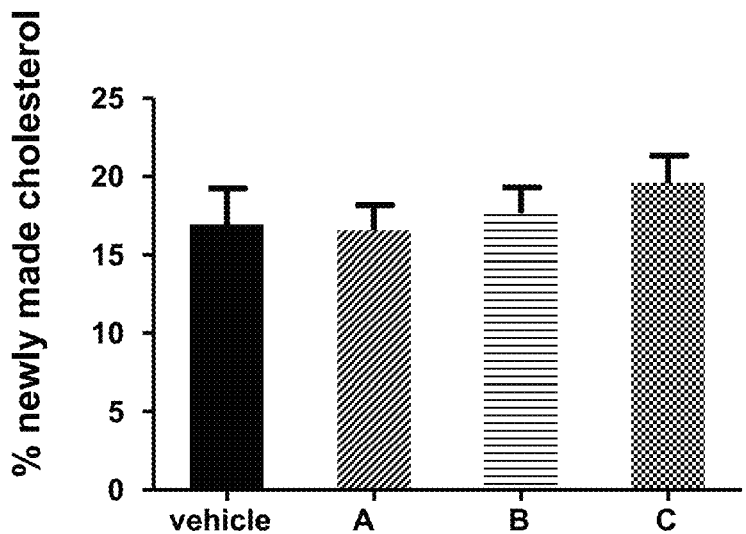
FIGS. 4A-C illustrate plasma levels of cholesterol (FIG. 4A) synthesis and lathosterol (FIG. 4B) as well as the ratio of lathosterol to cholesterol ratios (FIG. 4C) after sub-chronic treatment with vehicle or GRA Compounds A, B or C at 30 mpk QD for 5 days (n=8).
Figure 4B:
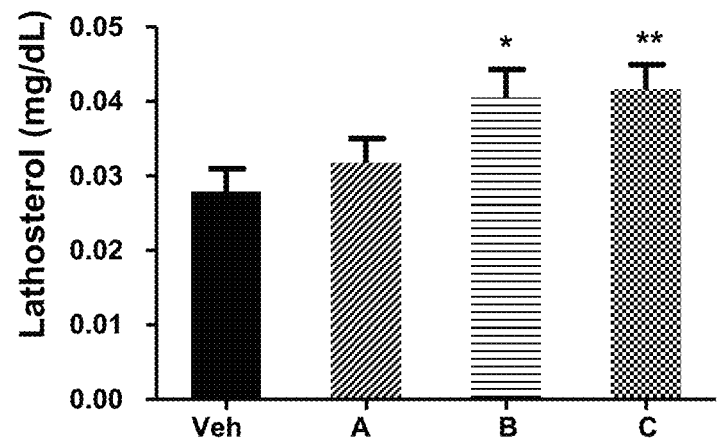
Figure 4C:
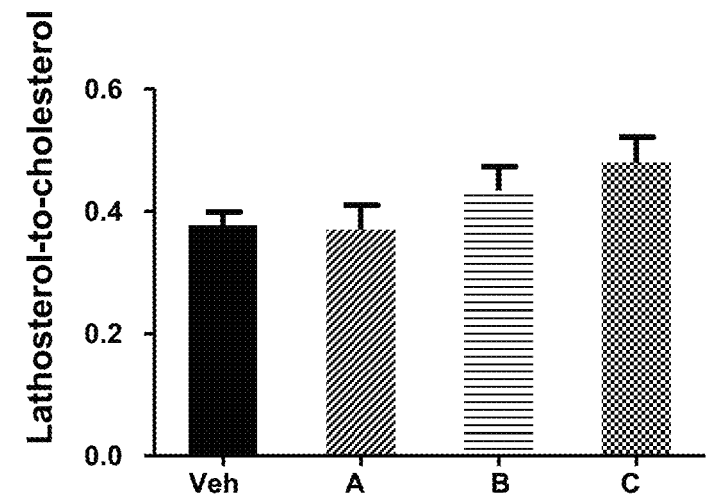

GRA Compounds A, B and C induced plasma total cholesterol in hGCGR mice after sub-chronic treatment with the compounds; see FIG. 2. In addition, plasma levels of phytosterols, campesterol and sitosterol were both significantly induced by Compounds A, B and C; see FIGS. 3A-B. In contrast, no significant effect was observed in either plasma level of lathosterol or cholesterol synthesis for Compound A while trends of increase were observed for Compound B and C; see FIGS. 4A-C.

EXAMPLE 2

Figure 5:
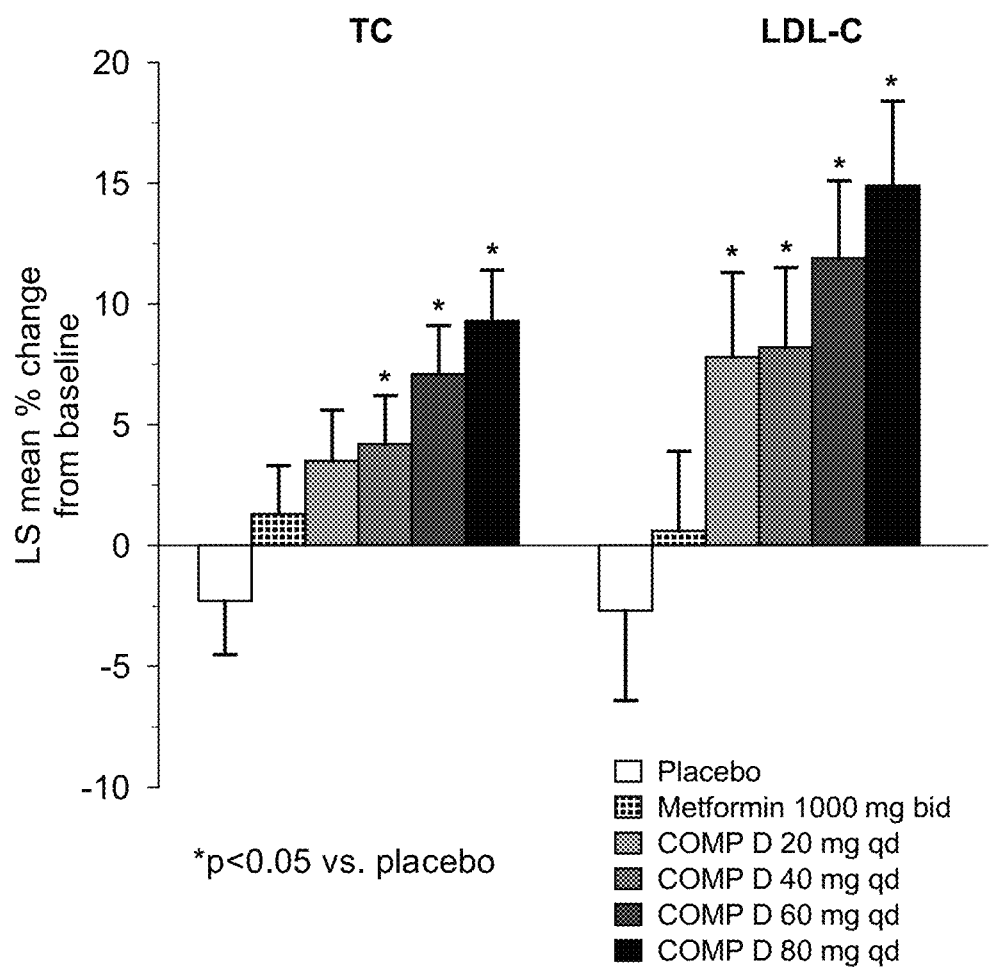
FIG. 5 illustrates plasma levels of total cholesterol and LDL-c in a human Phase 2b study of GRA Compound D. On the vertical axis is shown the statistical LS (Least Square) mean % change for placebo, metformin, and 20 mg, 40 mg, 60 mg and 80 mg doses of Compound D, respectively.
Figure 6:
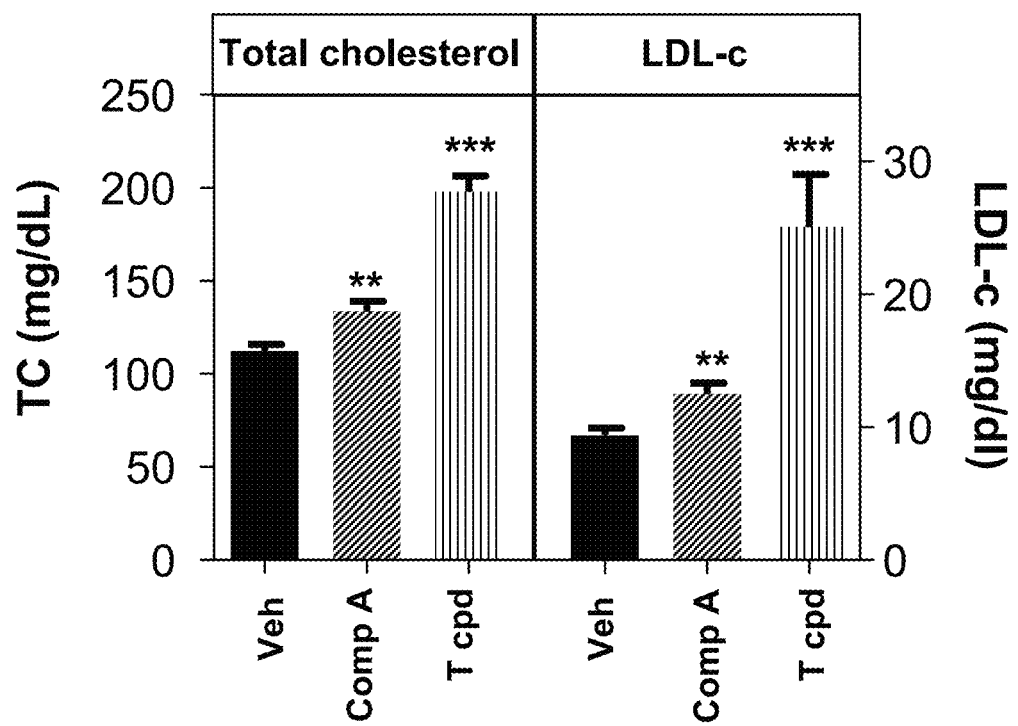
FIG. 6 illustrates plasma levels of total cholesterol and LDL-c in hGCGR mice following a 5 day treatment with GRA Compound A and positive control LXR agonist.

Similar Increase of Total Cholesterol and LDL-c Induced by Gras In Both Human and hGCGR In the human Phase 2 h studies of GRA Compound D, plasma levels of total cholesterol and LCL-c were dose-dependently increased by Compound D during the 12-wk trial. Treatment groups are shown in FIG. 5 and are from left to right: (i) Placebo, (ii) 1 g BID Metformin, (iii) 20 mg Compound D, (iv) 40 mg Compound D, (v) 60 mg Compound D and (vi) 80 mg Compound D. As shown in FIG. 5, the % changes in total cholesterol and LDL-c tracked with each other. In hGCGR mice treated with vehicle, Compound A (surrogate of Compound D), or Compound T (Genes and Development, 14:2831-2838, 2000, an LXR agonist used as a positive control), plasma levels of total cholesterol and LDL-c were significantly increased by Compound A and Compound T comparing with vehicle; see FIG. 6. It is important to note that lipoprotein profiles of mouse and human are fundamentally different. In mice, the major lipoproteins are in HDL while in humans the main lipoproteins are in LDL-c. In preclinical studies, hGCGR mice were used as the model for in vivo study. Plasma level of total cholesterol was used as a more reliable parameter to indicate the effect of GRAS on cholesterol metabolism.

EXAMPLE 3

Parallel Comparison of Different GrAS on Plasma Phytosterols of hGCGR Mice

Methods

The same protocol was used for this study as described previously. Briefly, male hGCGR mice at ~12 wks of age were treated with vehicle and GRA compounds Compound A, Compound F, Compound B, Compound C, Compound G, and Compound H. All compounds were dosed at 30 mpk QD for 5 days. Plasma total cholesterol, phytosterol, cholesterol absorption, and cholesterol synthesis were measured by using the same assays as described before.

Results

Figure 7A:
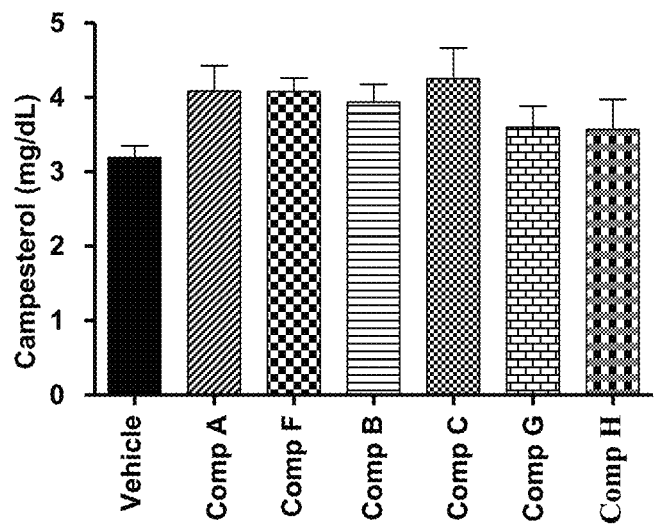
FIGS. 7A-C illustrate plasma levels of phytosterols campesterol (FIG. 7A) and sitosterol (FIG. 7B) individually, and combined (FIG. 7C), in hGCGR mice after sub-chronic treatment with vehicle and GRA compounds—Compound A, Compound F, Compound B, Compound C, Compound G and Compound H.
Figure 7B:
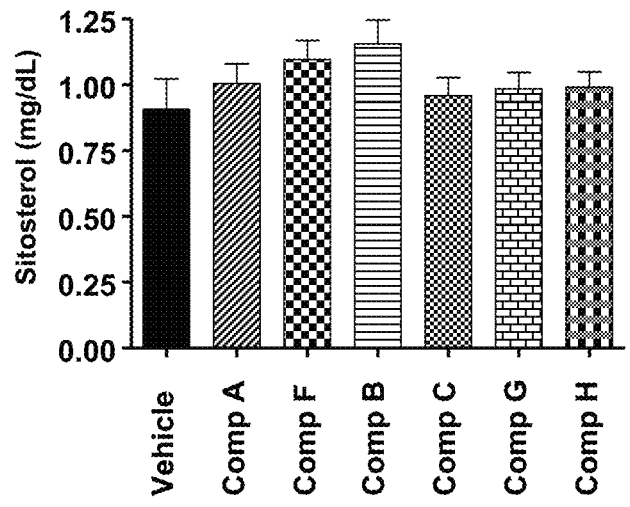
Figure 7C:
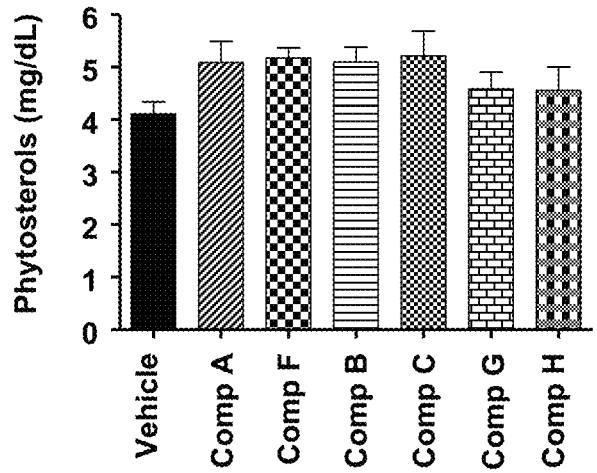

All GRA compounds—Compound A, Compound F, Compound B, Compound C, Compound G and Compound H showed an increase or a trend of increase in plasma phytosterols in hGCGR mice after sub-chronic treatment; see FIGS. 7A-C. Unlike humans, rodents are able to tightly maintain their plasma levels of total cholesterol and phytosterols. It is hard to develop phytosterolemnia in mice in all conditions. A relatively small increase of phytosterols in mice may translate to dramatic increase in humans.

EXAMPLE 4

Correlation of Plasma Phytosterols and Cholesterol Absorption in hGCGR Mice Dual Tracer Study for Cholesterol Absorption Methods Male hGCGR mice at ~12 wks of age maintained on chow or high cholesterol diet (n=8 group) were treated with vehicle and GRA Compound A@30 mpk QD for 9 days. Twenty four-hour feces before treatment and 3 days after treated were collected for fecal cholesterol characterization. On Day 4, mice were dosed with vehicle (0.5% MC, BID) or Compound A followed by administration with D6-cholesterol@15 mpk through p.o. and 13C-cholesterol@15 mpk through i.v. Blood was collected at 4, 24, 48, 72, and 96 h post injection by tail bleeding. For cholesterol synthesis, $D_2O$ was administered i.p. at 20 ml/kg on Day 7. On day 8, tail blood was collected for PK and mice were taken down for blood and liver collection. Plasma was isolated from blood by centrifuge at 8000 rpm for 5 min and submitted for GC/MS assay for cholesterol synthesis and absorption. Feces were sent to Taconic for fecal cholesterol assay. Asterisks denote statistical significance between treatment and vehicle groups. * $p<0.05$,  $p<0.01$, and * $p<0.001$ by ANOVA.

Results

Figure 8A:
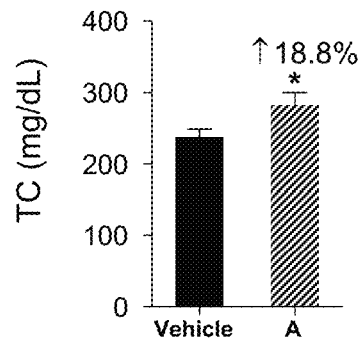
FIGS. 8A-C illustrate plasma total cholesterol (FIG. 8A), cholesterol synthesis (FIG. 8B) and cholesterol absorption (FIG. 8C) upon administration of GRA Compound A to male hGCGR mice.
Figure 8B:
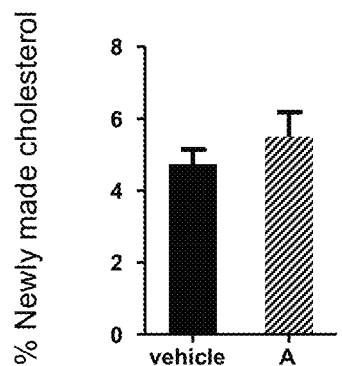
Figure 8C:
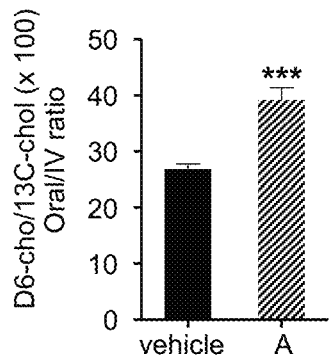

By using multiple tracers, a sub-chronic study was performed to determine the effect of Compound A on cholesterol synthesis, absorption, and excretion in hGCGR mice. A dual tracer study demonstrated that Compound A significantly increased plasma total cholesterol and cholesterol absorption; see FIGS. 8A and 8C. No change in cholesterol synthesis was observed; see FIG. 8B. This result confirmed the effect of Compound A on total cholesterol and cholesterol absorption, as indicated by measurement of plasma phytosterols above.

EXAMPLE 5

GRA-Induced Cholesterol Absorption is Associated with Blockage of GCGR

Methods

Male wild type and hGCGR mice on chow diet were treated with vehicle or GRA Compound D@3 and 10 mpk. On Day 1, mice were administered vehicle or Compound D followed by a glucagon-induced glucose tolerance test. On Day 5, mice were fasted at 7:30 am. After dosing at ~9:00 am, blood glucose was measured at 2-h post dose with a glucometer. At 6-h post dose, tail blood was collected for a PK measurement. Mice were euthanized with $CO_2$, and blood was collected by cardiac puncture. The liver was snap frozen in liquid nitrogen with a freezing clamp and saved in −80° C.

Plasma was isolated by centrifuging the blood at 8000 rpm for 5 min. Plasma level of total cholesterol was measured by an enzymatic colorimetric method (Wako Chemicals Inc.). Plasma levels of lathosterol and Phytosterol was measured by LC/MS.

Results

Figure 9A:
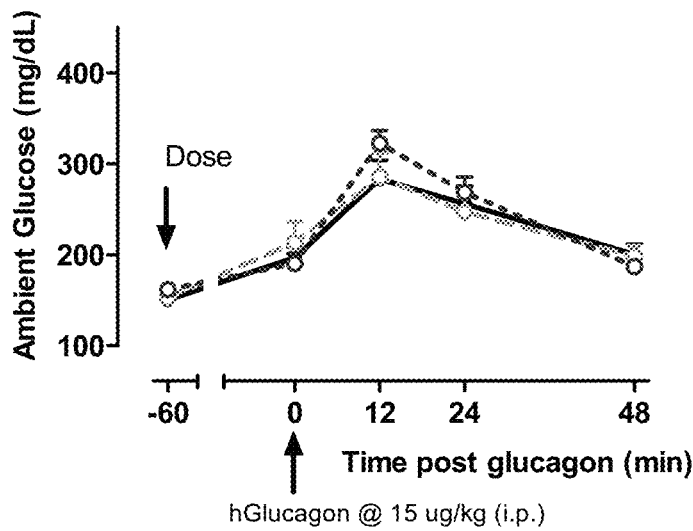
FIGS. 9A-B illustrate the effect of glucagon receptor antagonist compounds on a glucagon-induced glucose tolerance test ("GTT") in wild-type ("WT") mice (FIG. 9A) and hGCGR mice (FIG. 9B).
Figure 9B:
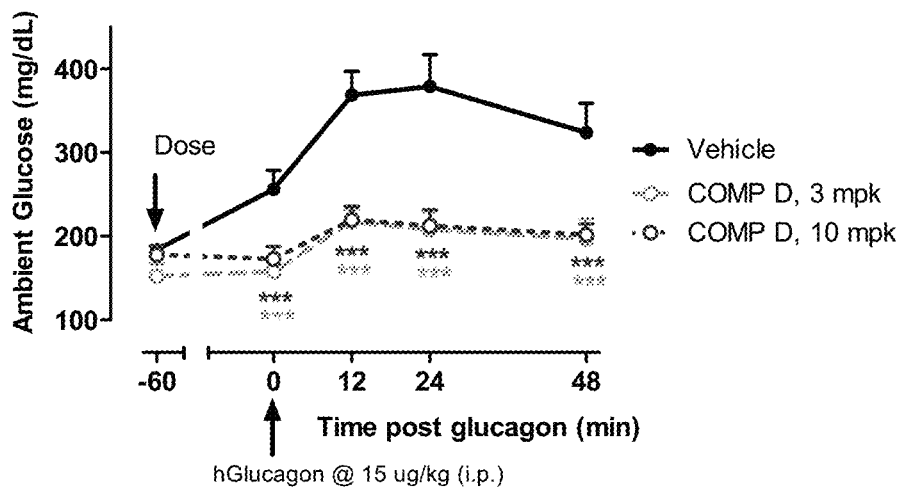
Figure 10A:
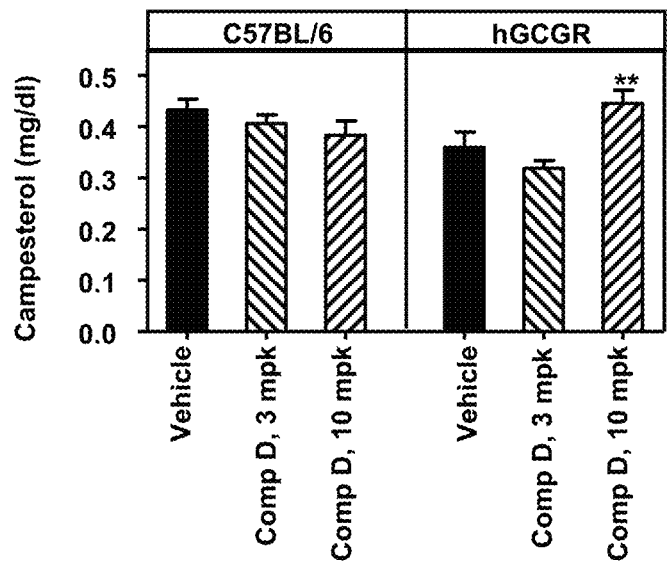
FIGS. 10A-B illustrate the effect of glucagon receptor antagonist compounds on plasma phytosterols, campesterol (FIG. 10A) and sitosterol (FIG. 10B).
Figure 10B:
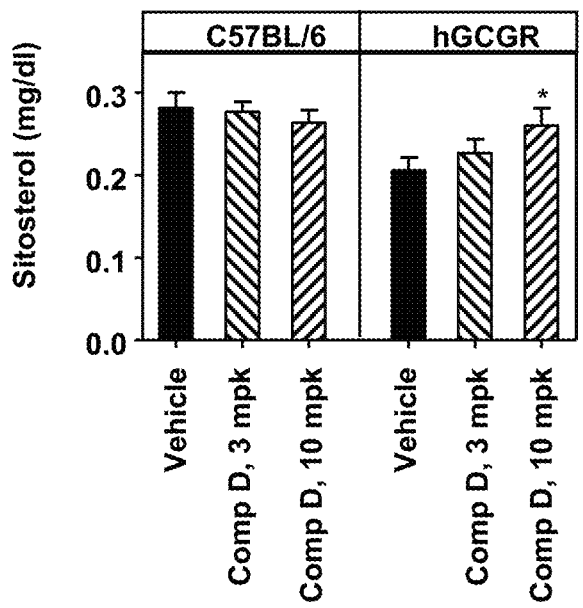

GRAs preferably block human GCGR over rodent GCGR. In this sub-chronic study of a parallel comparison of Compound D on cholesterol absorption in wild type versus hGCGR mice, Compound D suppressed glucagon-induced glucose excursion in hGCGR but not in wild type mice, indicating efficient blockage of GCGR in hGCGR but not wild type mice; see FIGS. 9A-B. Change in plasma phytosterols tracked with the blockage of GCGR, i.e. induction of phytosterols was only observed in hGCGR but not wild type mice; see FIGS. 10A-B. This result suggests that GRAs-induced cholesterol absorption is associated with blockage of GCGR, which is in line with the result of the phase 2a clinical studies of Compound E.

EXAMPLE 6

GRA Compound D Induced Plasma Phytosterols in Type 2 Diabetic Patients

Methods

Human serum samples of GRA Compound D phase 2 b trial were obtained for post hoc analysis of plasma hiomarkers of cholesterol absorption. Type 2 diabetic patients were treated with placebo, and Compound D@20, 40, 60, and 80 mg for 12 wks followed by 3 wks of washout. Treatment groups placebo (n=8), Compound D@60 mg (n=46), and Compound D@80 mg (n=16) were analyzed for plasma campesterol and sitosterol by LC/MS. Asterisks denote statistical significance of % change of parameters at wk 12 post treatment versus baseline. * $p<0.05$,  $p<0.01$, and * p 0.001 by ANOVA.

Results

Figure 11A:
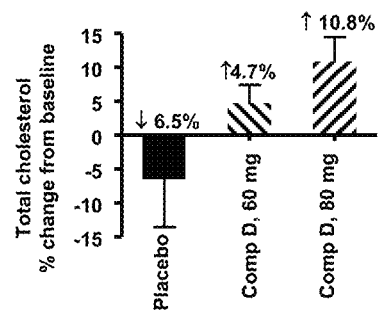
FIGS. 11A-C illustrate the % change of plasma levels of total cholesterol (FIG. 11A), and phytosterols campesterol (FIG. 11B) and sitosterol (FIG. 11C) in type 2 diabetic patients treated with GRA Compound D.
Figure 11B:
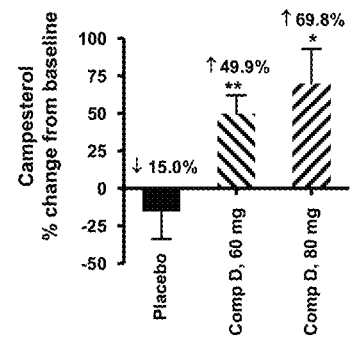
Figure 11C:
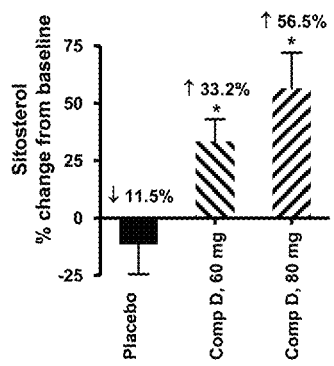

Plasma phytosterols have been used as a hiomarker of cholesterol absorption in human. Ezetimihe has been demonstrated to significantly decrease plasma levels of phytosterols in human trials. Herein Compound D dose-dependently increased plasma levels of total cholesterol and LDL-c in type 2 diabetic patients; see FIG. 11A. It showed a similar increase in plasma levels of campesterol and sitosterol, indicating induction of cholesterol absorption in human; see FIGS. 11B-C. This finding is consistent with the translatability of cholesterol absorption across species from mice to human, which had been demonstrated during the discovery of ezetimibe.

EXAMPLE 7

Normal Range of Average LDL-C Levels in Type 2 Diabetic Patients in Phase 2B Trial of Compound D Methods In phase 2b trial studies of Compound D, the average plasma levels of LDL-c in the placebo, Compound D@20, 40, 60, 80 mg, and metformin@2 g groups were 112.3, 117.7, 117.3, 110.0, 111.9, and 113.8 mg/dl at baseline, respectively. Plasma levels of LDL-c of the majority of the patients were within the normal range (≤130 mg/dl) according to the guideline of the American Heart Association and Mayo Clinic. After 12-week treatment, the average plasma levels of LDL-c were 105.4, 117.7, 123.2, 119.7, 126.6, and 111.1 mg/dl, respectively.

The following table illustrates the plasma levels of LDL-c in the patients in the phase 2b trial of Compound D. Type 2 diabetic patients with fasting glucose level of 140 to 240 mg/dl were recruited to the phase 2b trial of Compound D. After a 6-wk washout of any previous anti-hyperglycemic agents, patients were treated with placebo, Compound D QD@20, 40, 60, and 80 mg, and metformin BID@1 g for 12 wks. Values in bold are the percentage of patients on Day-1 and wk 12 less than or equal to the designated cutoff values at 130, 110, 100, and 70 mg/dl.

|  | Day −1 | | | | Wk 12 | | | |
| --- | --- | --- | --- | --- | --- | --- | --- | --- |
| Treatment | 130 mg/dl | 110 mg/dl | 100 mg/dl | 70 mg/dl | 130 mg/dl | 110 mg/dl | 100 mg/dl | 70 mg/dl |
| Placebo | 64.1 | 46.2 | 35.9 | 7.7 | 84.6 | 53.8 | 38.5 | 17.9 |
| Comp D 20 mg | 65.1 | 39.5 | 32.6 | 9.3 | 65.1 | 44.2 | 27.9 | 9.3 |
| Comp D 40 mg | 61.9 | 40.5 | 31.0 | 9.5 | 64.3 | 40.5 | 33.3 | 7.1 |
| Comp D 60 mg | 78.3 | 52.2 | 45.7 | 10.9 | 65.2 | 43.5 | 32.6 | 2.2 |
| Comp D 80 mg | 78.6 | 52.4 | 42.9 | 9.5 | 59.5 | 40.5 | 31.0 | 7.1 |
| Metformin | 70.8 | 54.2 | 41.7 | 6.3 | 70.8 | 54.2 | 45.8 | 2.1 |

Results

Figure 12A:
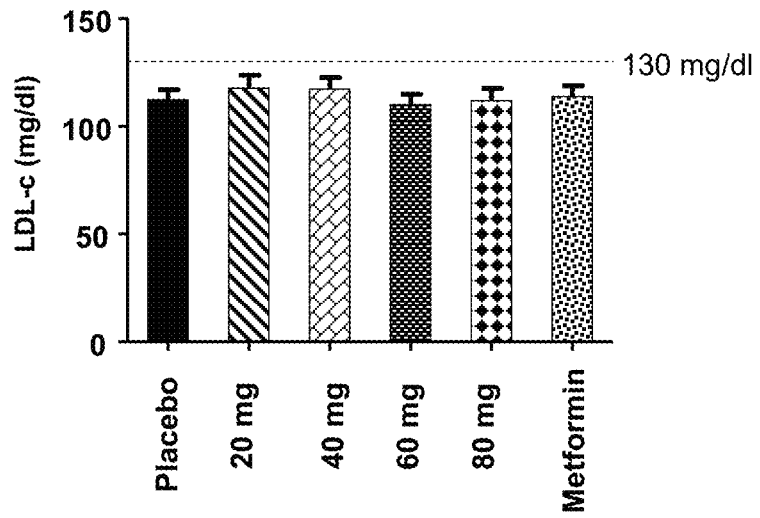
FIGS. 12A-B illustrate plasma levels of LDL-c in type 2 diabetic patients treated with placebo, GRA Compound D or metformin at Day 1 (FIG. 12A) and Week 12 (FIG. 12B).
Figure 12B:
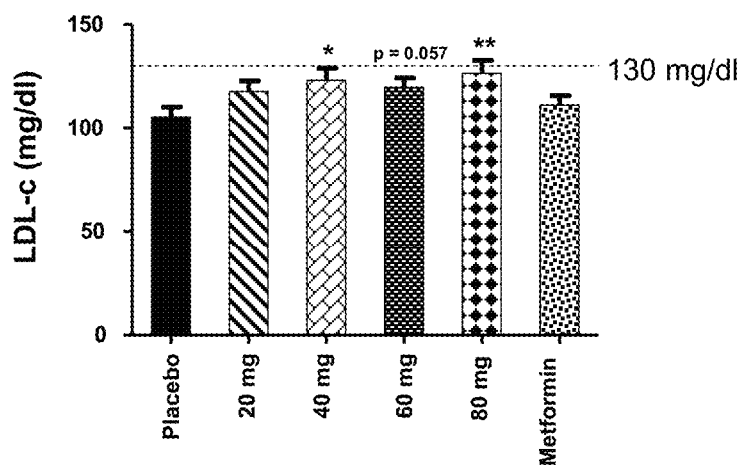
Figure 13A:
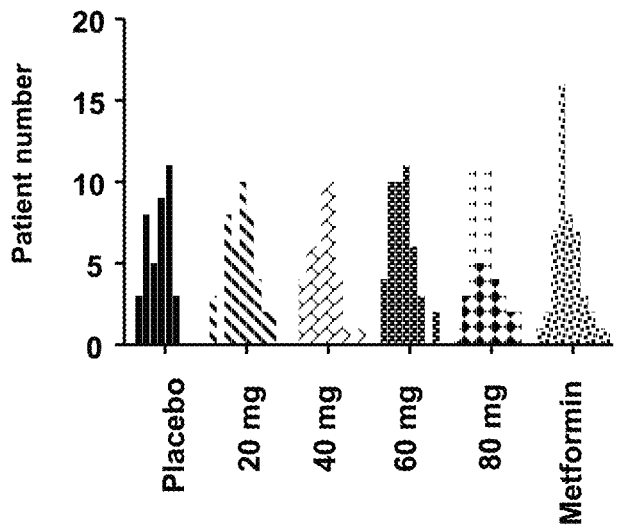
FIGS. 13A-B illustrate the level of LDL-c distribution frequency in type 2 diabetic patients treated with placebo, GRA Compound D or metformin at Day 1 (FIG. 13A) and Week 12 (FIG. 13B).
Figure 13B:
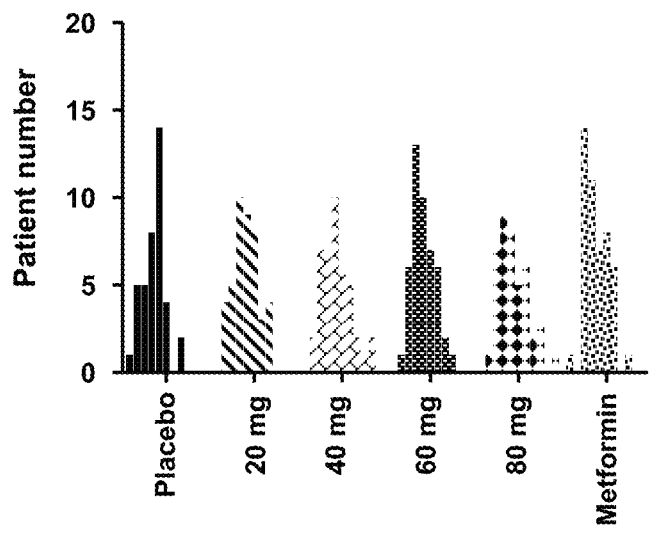
Figure 14A:
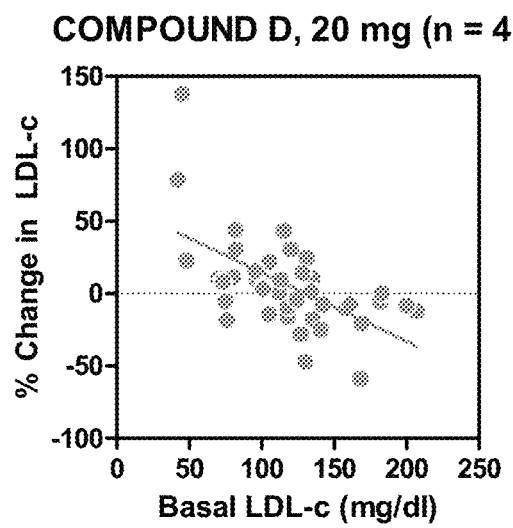
FIGS. 14A-D illustrate the baseline plasma level of LDL-c (Day-1) in patients plotted with the % change of LDL-c at week 12 from baseline following treatment with GRA Compound D. Compound D was administered at 20 mg (n=43.
Figure 14B:
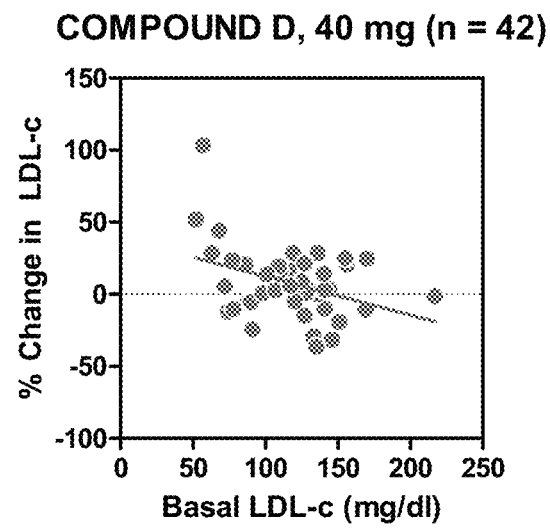
Figure 14C:
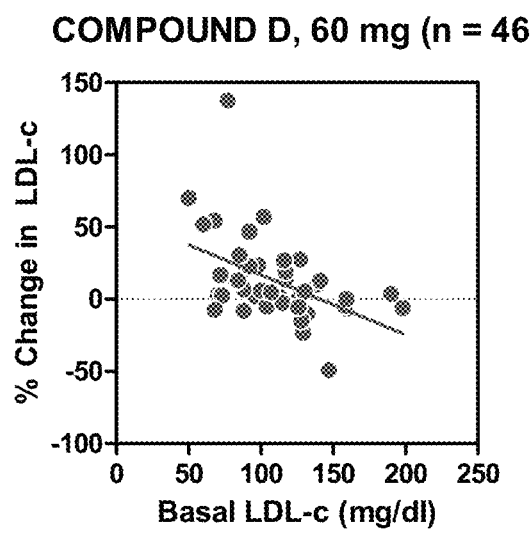
Figure 14D:
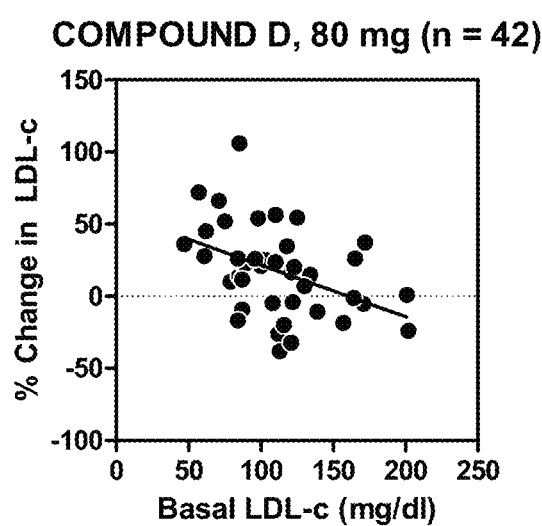

The average plasma levels of LDL-c of the patients recruited for the phase 2b trial of Compound D were 110-117.7 mg/dl prior to treatment, and 105.4-126.6 mg/dl post treatment; see FIGS. 12A-B. According to the guidelines of LDL-c from American Heart Association and Mayo Clinic, LDL-c of 130 mg/dl is the cutoff value for definition of normal or near normal LDL-c. The average levels of LDL-c of these patients were under the borderline high level of LDL-c (130 mg/dl). In each group of the trial, the level of LDL-c was distributed normally as indicated by distribution frequency; see FIGS. 13A-B.

Further patient analysis by setting the cutoff values at 130, 110, 100, and 70 mg/dl demonstrated that the majority of patients for the Compound D trial were under 130 mg/dl both prior to and post the 12-wk treatment in all groups. All the patients recruited for the trial were diagnosed as hyperglycemic with type 2 diabetes, however, the majority of the patients had normal or near normal plasma LDL-c and thus were not qualified as hypercholesterolemic. Comparing with placebo and metformin, Compound D dose-dependently increased LDL-c after 12-week treatment, although the increases were relatively small (from 7.2% at 20 mg to 16.7% at 80 mg, versus placebo −3.1% and metformin 2.2%). Prevention of any lipid side effect of GRAs by the described method of co-administering a cholesterol absorption inhibitor like Zetia® should benefit cardiovascular complications in the long run.

EXAMPLE 8

Negative Correlation Between Baseline LDL-C and % Change in LDL-C in Compound D Trial The baseline plasma level of LDL-c (Day -1) was plotted with the % change of LDL-c at week 12 from baseline. As shown in FIGS. 14A-D, there is a negative correlation between the two parameters for Compound D at all doses. Patients with relatively lower plasma levels of LDL-c are more likely to be more prone to increase LDL-c after chronic treatment of Compound D. In contrast, patients with relatively higher LDL-c showed less or no increase of LDL-c after 12-wk treatment of Compound D. This observation indicates that combining cholesterol absorption inhibitors, like ezetimibe, with glucagon receptor antagonists, like Compound D, is more appropriate for patients with normal plasma levels of LDL-c.

EXAMPLE 9

Combination Treatment of GRAS with Ezetimibe Prevented GRA-Induced Hypercholesterolemia in hGCGR Mice Methods A similar protocol was deployed in this part of work except ezetimibe was added to the combination treatment groups. Briefly, male hGCGR mice at ~12 wks of age were treated with vehicle, ezetimibe@10 mpk, Compound A@30 mpk, Compound D@30 mpk, Compound E@30 mpk, Compound A@30 mpk+ezetimibe@10 mpk, Compound D@30 mpk+ezetimibe@10 mpk, Compound E@30 mpk+ezetimibe@10 mpk. Plasma total cholesterol, phytosterol, cholesterol absorption, and cholesterol synthesis were quantified using the same assays as described before.

Results

Figure 15A:
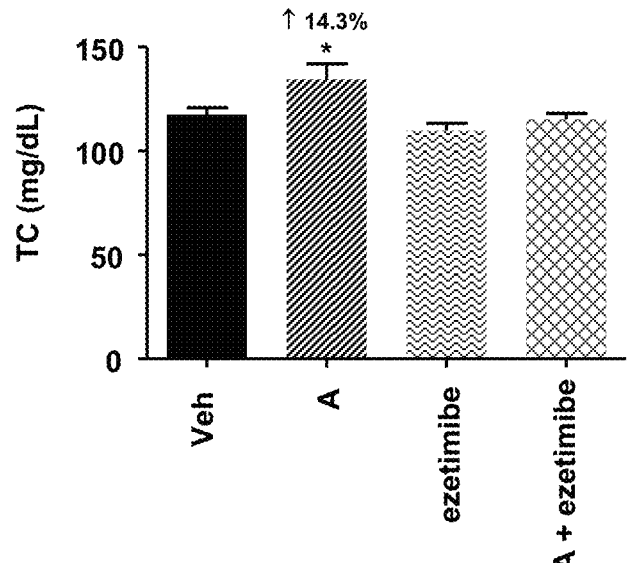
FIGS. 15A-B illustrate total plasma cholesterol (FIG. 15A) and cholesterol absorption (FIG. 15B) upon sub-chronic treatment of hGCGR mice with vehicle. GRA Compound A (30 mpk), ezetimibe (10 mpk), or Compound A (30 mpk)+ezetimibe (10 mpk) QD for 9 days.
Figure 15B:
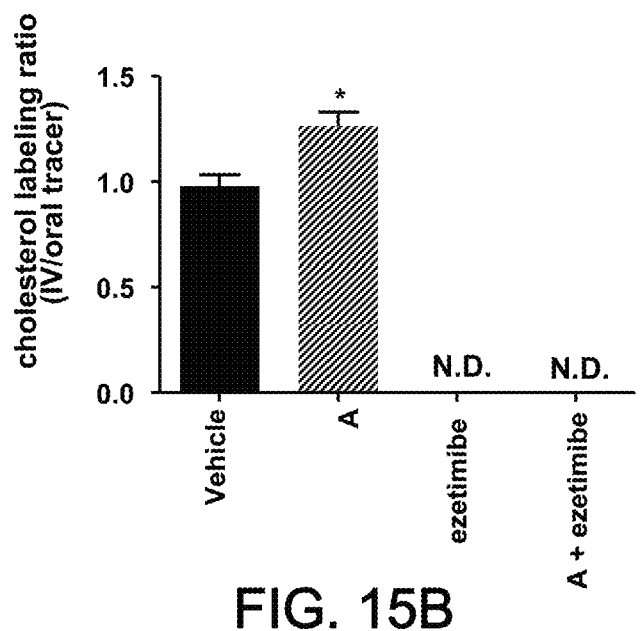
Figure 16A:
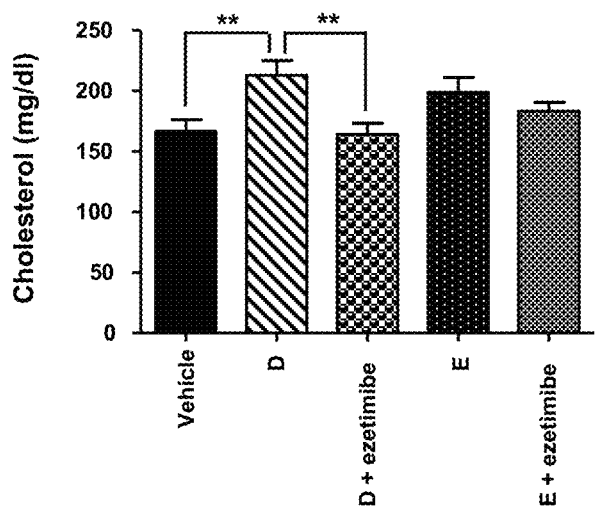
FIGS. 16A-B illustrate total plasma cholesterol (FIG. 16A) and cholesterol absorption (FIG. 16B) upon sub-chronic treatment of hGCGR mice with vehicle, GRA Compound D (30 mpk), Compound E (30 mpk), Compound D (30 mpk)+ezetimibe (10 mpk), or Compound E (30 mpk)+ezetimibe (10 mpk) QD for 9 days.
Figure 16B:
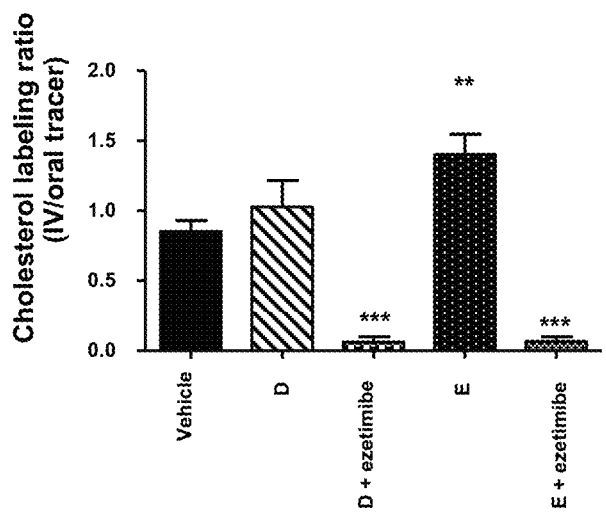

Glucagon receptor antagonist compounds A, D and E significantly increased or tended to increase plasma total cholesterol and cholesterol absorption in hGCGR mice after sub-chronic treatment; see FIGS. 15A-B (for Compound A) and FIGS. 16A-B (tor Compounds D and E). Combining with ezetimibe prevented the induction of total cholesterol and cholesterol absorption caused by GRAS. This body of work indicates the feasibility of combination treatment of GRAs and cholesterol absorption inhibitors such as ezetimibe to avoid any lipid side effect.

EXAMPLE 10

Statins Treatment Did Not Prevent GRA Compound D-Induced Elevation of LDL-C

Figure 17:
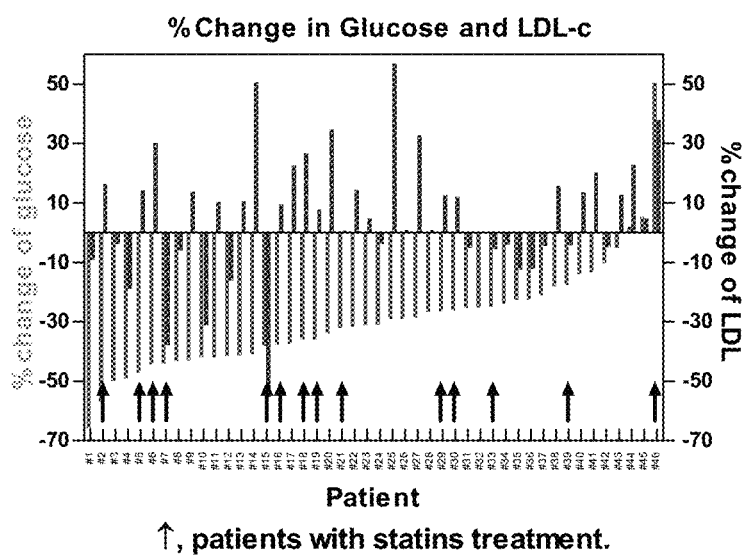
FIG. 17 illustrates the lack of a correlation observed between 5 changes in glucose and LDL-c despite the presence of a statin in patients being treated with Compound D (↑ indicates the presence of a statin). Furthermore, 9 out of the 14 patients with statins treatment during the trial showed elevation of LDL-c.

In the 46 patients on Compound D@60 mg in the phase 2b trial, 14 patients were on statins during the 12-wk trial. While there was a substantial reduction in blood glucose levels in most patients, there was no correlation observed between % change in glucose and. LDL-c (despite the presence of the statin); see FIG. 17. More importantly, 9 out of 14 patients with statins treatment during the trial showed elevation of LDL-c. This result indicates that combining glucagon receptor antagonists (like Compound D) with statins may not correct any associated lipid increase in most type 2 diabetic patients.

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A method of treating diabetes in a mammalian subject having an LDL cholesterol plasma level of less than 100 mg/dL, which comprises administering to said mammalian subject:
   (a) a glucagon receptor antagonist, and
   (b) a cholesterol absorption inhibitor,
wherein the subject is not further being treated with a statin.

2. The method of claim 1 wherein the glucagon receptor antagonist compound and the cholesterol absorption inhibitor compound are present in a single dosage form.

3. The method of claim 2 wherein the glucagon receptor antagonist compound and the cholesterol absorption inhibitor compound are in a bilayer tablet.

4. The method of claim 1 wherein the glucagon receptor antagonist compound and the cholesterol absorption inhibitor compound are present each in a separate dosage form for simultaneous or sequential administration.

5. The method of claim 1 for treating type 2 diabetes.

6. The method of claim 1 wherein the cholesterol absorption inhibitor compound is:

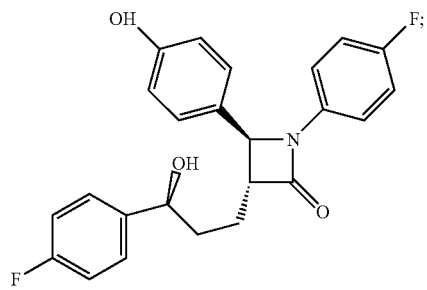 [SMILES: O=C1[C@H](CC[C@H](O)c2ccc(F)cc2)[C@@H](c2ccc(O)cc2)N1c1ccc(F)cc1]

or a pharmaceutically acceptable salt thereof.

7. The method of claim 1 wherein the glucagon receptor antagonist compound is a compound selected from the following table of compounds:

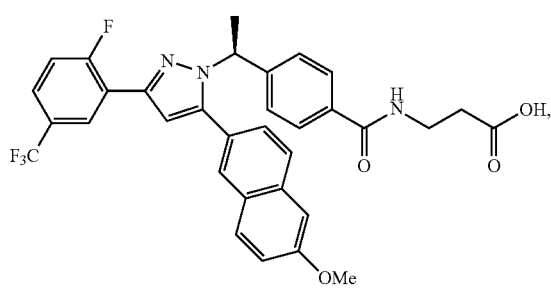

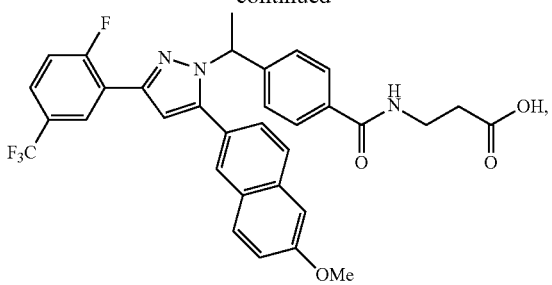

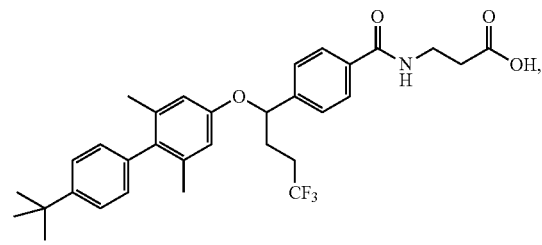

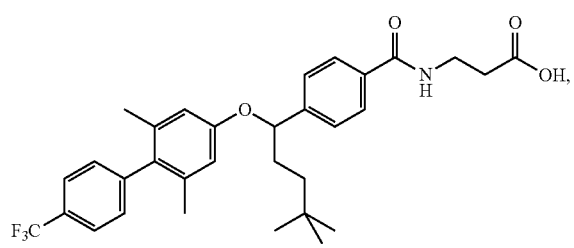

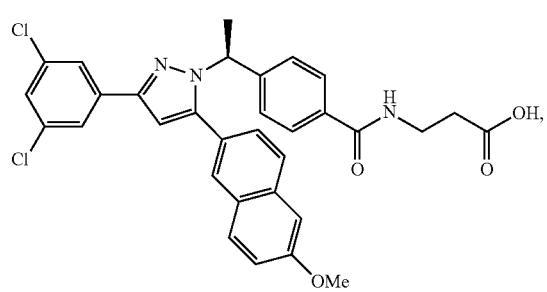

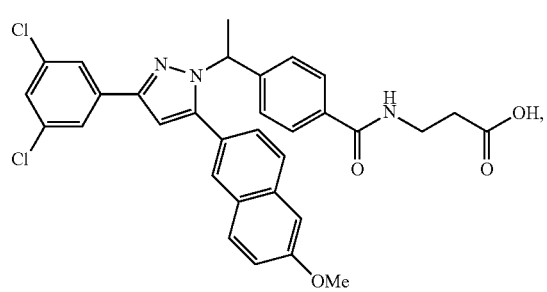

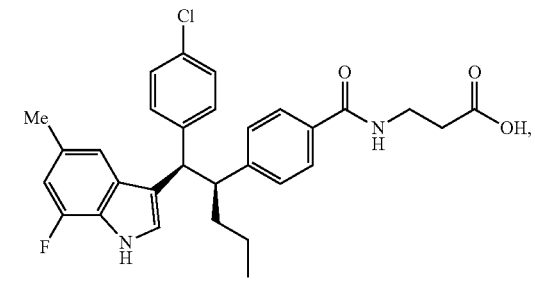

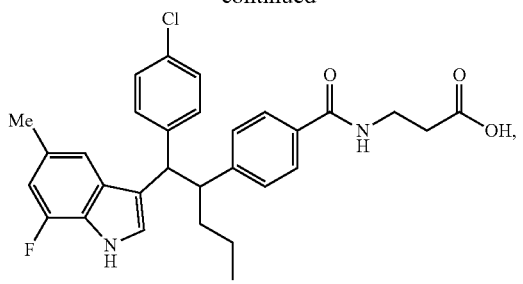
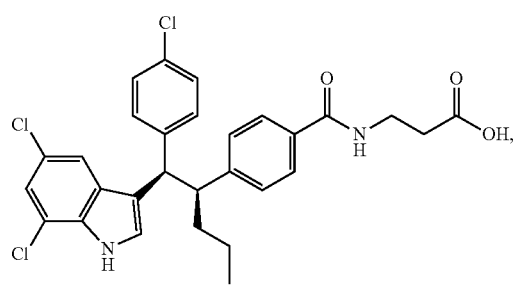
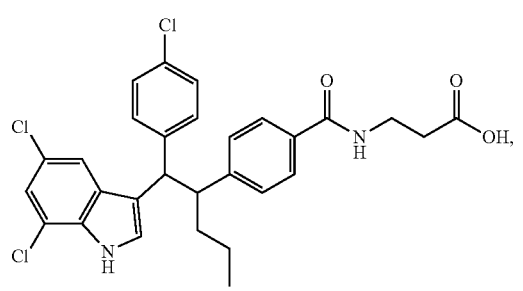
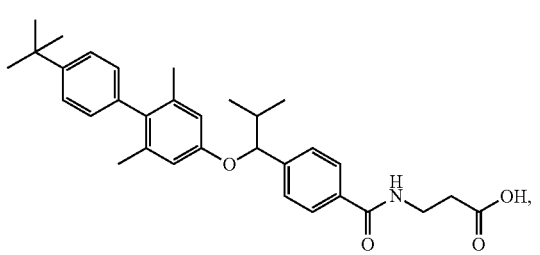
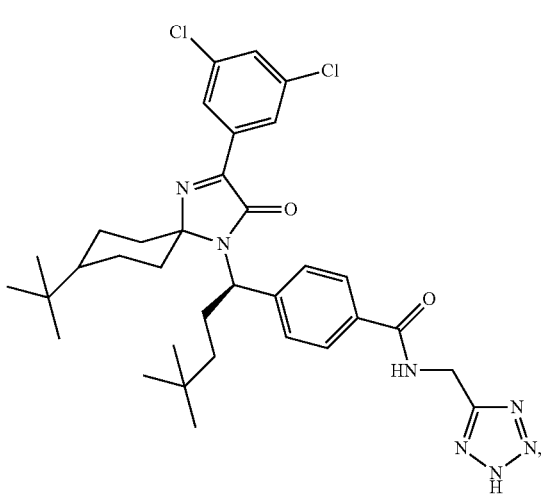
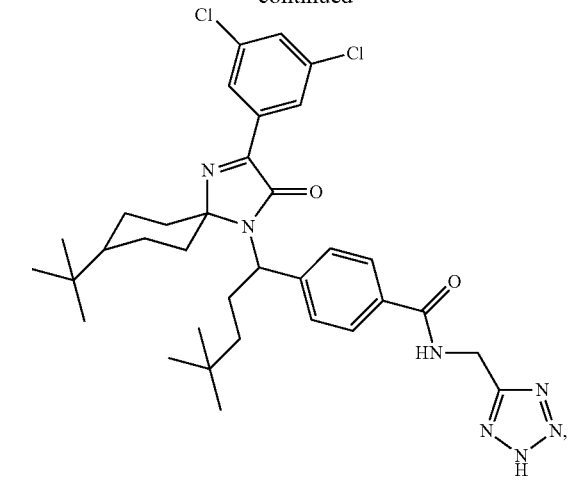
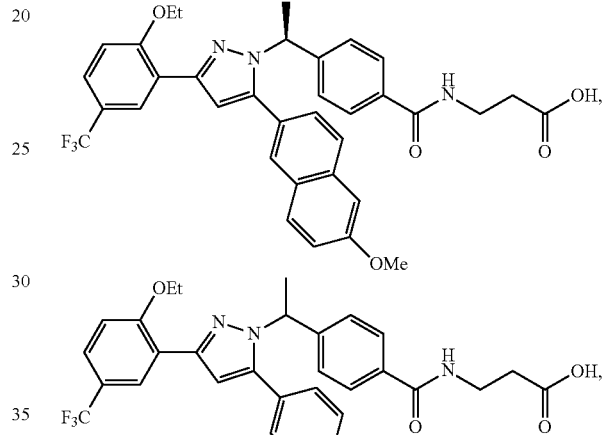
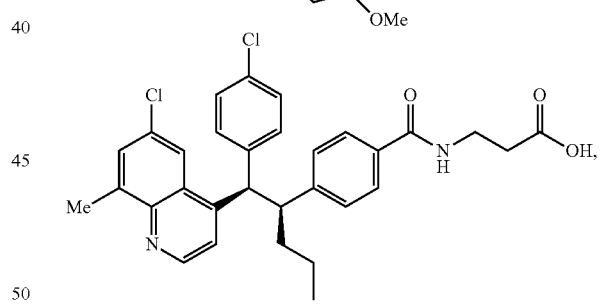
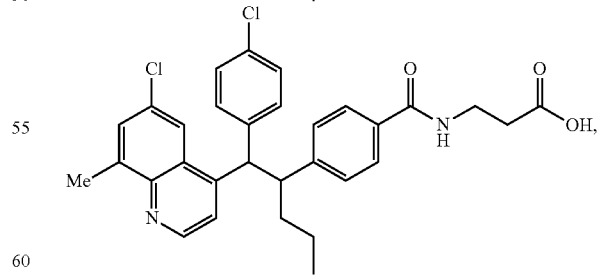
or a pharmaceutically acceptable salt thereof.
8. The method of claim 1 wherein the mammalian subject is a human.
9. The method of claim 6 wherein the mammalian subject is a human.

10. The method of claim 7 wherein the mammalian subject is a human.

11. The method of claim 1 wherein the glucagon receptor antagonist compound is:

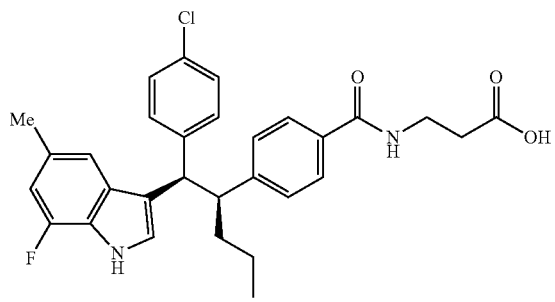 [SMILES: CCC[C@H](c1ccc(C(=O)NCCC(=O)O)cc1)[C@H](c1ccc(Cl)cc1)c1c[nH]c2c(F)cc(C)cc12]

or a pharmaceutically acceptable salt thereof.

12. The method of claim 6 wherein the glucagon receptor antagonist compound is:

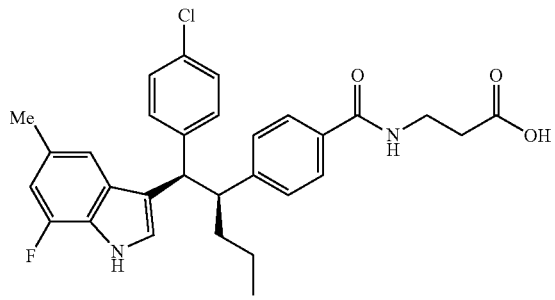 [SMILES: CCC[C@H](c1ccc(C(=O)NCCC(=O)O)cc1)[C@H](c1ccc(Cl)cc1)c1c[nH]c2c(F)cc(C)cc12]

or a pharmaceutically acceptable salt thereof.

13. The method of claim 1 wherein the glucagon receptor antagonist compound is:

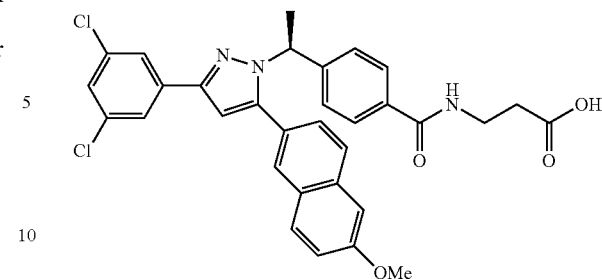

or a pharmaceutically acceptable salt thereof.

14. The method of claim 6 wherein the glucagon receptor antagonist compound is:

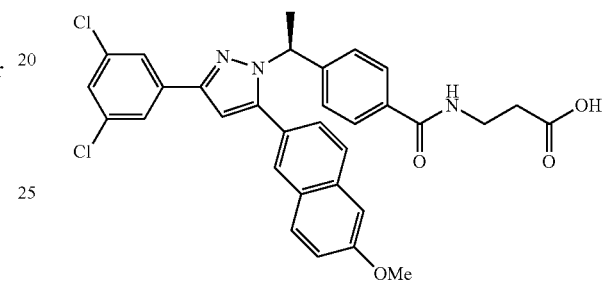

or a pharmaceutically acceptable salt thereof.

15. A method of reducing hyperglycemia in a mammalian subject having an LDL cholesterol plasma level of less than 100 mg/dL, which comprises administering to said mammalian subject:
  (a) a glucagon receptor antagonist, and
  (b) a cholesterol absorption inhibitor,
wherein the subject is not further being treated with a statin.

* * * * *

UNITED STATES PATENT AND TRADEMARK OFFICE
CERTIFICATE OF CORRECTION

Page 1 of 1

PATENT NO. : 11,077,092 B2
APPLICATION NO. : 15/484508
DATED : August 3, 2021
INVENTOR(S) : Guan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 141 days.

Signed and Sealed this
Twenty-fourth Day of January, 2023

Katherine Kelly Vidal
*Director of the United States Patent and Trademark Office*